United States Patent [19]
Stanley et al.

[11] Patent Number: 5,139,023
[45] Date of Patent: Aug. 18, 1992

[54] APPARATUS AND METHOD FOR NONINVASIVE BLOOD GLUCOSE MONITORING

[75] Inventors: Theodore H. Stanley; Charles D. Ebert; William I. Higuchi; Jie Zhang, all of Salt Lake City, Utah

[73] Assignees: TheraTech Inc.; Stanley Research Foundation, both of Salt Lake City, Utah

[21] Appl. No.: 360,876

[22] Filed: Jun. 2, 1989

[51] Int. Cl.$^5$ .............................................. A61B 5/00
[52] U.S. Cl. ..................... 128/637; 128/760; 128/763; 128/768; 604/289; 604/290
[58] Field of Search ............... 128/760, 767, 632, 637, 128/763; 604/289, 290, 304, 307, 20, 896; 514/975

[56] References Cited

U.S. PATENT DOCUMENTS

| | | |
|---|---|---|
| 2,561,071 | 7/1951 | Prisk .................................... 128/260 |
| 3,053,255 | 9/1962 | Meyer .................................. 128/268 |
| 3,289,671 | 12/1966 | Troutman et al. ................... 128/2.1 |
| 3,323,774 | 6/1967 | Wilson ................................. 251/125 |
| 3,794,910 | 2/1974 | Ninke et al. ...................... 324/30 R |
| 4,014,334 | 3/1977 | Theeuwes et al. ................. 128/260 |
| 4,116,241 | 9/1978 | Theeuwes et al. ................. 128/260 |
| 4,151,832 | 5/1979 | Hamer ................................ 128/765 |
| 4,190,060 | 2/1980 | Greenleaf et al. ................. 128/760 |
| 4,200,110 | 4/1980 | Peterson et al. ................... 128/634 |
| 4,250,163 | 2/1981 | Nagai et al. ......................... 424/14 |
| 4,292,299 | 9/1981 | Suzuki et al. ........................ 424/16 |
| 4,321,252 | 3/1982 | Keith et al. ........................... 604/28 |
| 4,325,367 | 4/1982 | Tapper ............................ 128/207.21 |
| 4,364,385 | 12/1982 | Lossef ............................. 128/213 R |
| 4,379,454 | 4/1983 | Campbell et al. ................... 604/897 |
| 4,380,454 | 4/1983 | Campbell et al. ................... 604/897 |
| 4,398,543 | 8/1983 | Sandlin et al. ...................... 128/760 |
| 4,401,122 | 8/1983 | Clark, Jr. ............................. 128/635 |

(List continued on next page.)

FOREIGN PATENT DOCUMENTS

| | | | |
|---|---|---|---|
| 8600536 | 1/1986 | World Int. Prop. O. | ......... 604/307 |
| 9002511 | 3/1990 | World Int. Prop. O. | ......... 128/760 |

OTHER PUBLICATIONS

Aungst, Bruce J. et al, "Comparison of Nasal, Rectal, Buccal, Sublingual and Intramuscular Insulin Efficacy and the Effects of a Bile Salt Absorption Promoter", The Journal of Pharmacology and Experimental Therapeutics, vol. 244, No. 1, pp. 23-27 (1988).

(List continued on next page.)

*Primary Examiner*—C. Fred Rosenbaum
*Assistant Examiner*—Chalin Smith
*Attorney, Agent, or Firm*—Workman, Nydegger & Jensen

[57] ABSTRACT

The present invention is directed to novel methods and apparatus for noninvasive blood glucose monitoring. Blood glucose is monitored noninvasively by correlation with amount of glucose which permeates an epithelial membrane, such as skin or a mucosal membrane, into a glucose receiving medium over a specified time period. The glucose receiving medium preferably includes a glucose permeation enhancer capable of increasing the glucose permeability across the epithelial membrane. The glucose receiving medium is positioned against the epithelial membrane so that the permeation enhancer alters the permeability of the membrane. After sufficient time delay, the glucose receiving medium is removed and analyzed for the presence of glucose using conventional analytical techniques.

The apparatus within the scope of the present invention includes means for supporting the glucose receiving medium. Such means for supporting the glucose receiving medium may include a housing defining a receiving chamber therein which holds the glucose receiving medium and an opening to the receiving chamber. The means for supporting the glucose receiving medium may also include a hydrogel. The apparatus also preferably includes means for temporarily positioning the glucose receiving medium against the epithelial membrane.

62 Claims, 19 Drawing Sheets

U.S. PATENT DOCUMENTS

| | | | |
|---|---|---|---|
| 4,457,748 | 7/1984 | Lattin et al. | 604/20 |
| 4,458,686 | 7/1984 | Clark, Jr. | 128/635 |
| 4,538,616 | 9/1985 | Rogoff | 128/632 |
| 4,542,750 | 9/1985 | Ettare | 128/760 |
| 4,542,751 | 9/1985 | Webster et al. | 128/760 |
| 4,548,922 | 10/1985 | Carey et al. | 514/4 |
| 4,557,723 | 12/1985 | Sibalis | 604/20 |
| 4,573,996 | 3/1986 | Kwiatek et al. | 604/897 |
| 4,622,031 | 11/1986 | Sibalis | 604/20 |
| 4,635,488 | 1/1987 | Kremer | 73/864.72 |
| 4,640,689 | 2/1987 | Sibalis | 604/20 |
| 4,671,953 | 6/1987 | Stanley et al. | 424/440 |
| 4,690,683 | 9/1987 | Chien et al. | 604/896 |
| 4,693,711 | 9/1987 | Bremer et al. | 604/306 |
| 4,706,676 | 11/1987 | Peck | 128/632 |
| 4,710,191 | 12/1987 | Kwiatek et al. | 604/897 |
| 4,723,958 | 2/1988 | Pope et al. | 604/890 |
| 4,743,249 | 5/1988 | Loveland | 424/447 |
| 4,746,508 | 5/1988 | Carey et al. | 424/88 |
| 4,747,841 | 5/1988 | Kuratomi et al. | 604/291 |
| 4,819,645 | 4/1989 | Peck | 128/760 |
| 4,889,721 | 12/1989 | Ueda et al. | 424/449 |
| 4,892,737 | 1/1990 | Bodor et al. | 424/449 |
| 4,909,256 | 3/1990 | Peck | 128/760 |
| 4,957,108 | 9/1990 | Schoendorfer et al. | 128/632 |

OTHER PUBLICATIONS

Banga, Ajay K. et al., "Systematic Delivery of Therpeutic Peptides and Proteins", International Journal of Pharmaceutics 48, pp. 15–50 (1988).

Ishida, Masami, "New Muycosal Dosage Form of Insulin", Chemical Pharmaceutical Bulletin, vol. 29, pp. 810–816 (1982).

Machol, Libby, "Innovative Ways to Administer Drugs", Technology (1989), pp. 85–103.

Micossi, P. et al., "Free-Insulin Profiles After Intraperitoneal, Intramuscular and Subcutaneous Insulin Administration, " Diabetes Care, vol. 9, No. 6, pp. 575–578 (Nov.–Dec. 1986).

Mishima, Motohiro et al., "Studies on the Promoting Effects of Mediuym Chain Fatty Acid Salts on the Nasal Absorption of Insulin in Rats," Journal of Pharmacobiodynamics, vol. 10, pp. 624–631 (1987).

Robinson, Joseph R., "Mucoadhesive Drug Delivery Systems: Buccal Drug Delivery, Potential Close to Fruition?" Welcome Trends in Hospital Pharmacy, pp. 8–12 (Jan. 1989).

"Conrex Pharmaceutical Advances Drug Delivery Methods".

APPARATUS AND METHOD FOR NONINVASIVE BLOOD GLUCOSE MONITORING

BACKGROUND

1. The Field of the Invention

The present invention is directed to methods and apparatus for monitoring blood constituents. More particularly, blood constituents such as glucose, are monitored noninvasively through diffusion across epithelial membranes.

2. Technology Review

The blood is routinely tested for various blood constituents in countless medical procedures. This typically involves drawing an actual blood sample from the patient, followed by blood analysis. Most people can tolerate giving an occasional blood sample, but continually drawing blood for analysis creates additional safety risks for the patient. For those persons suffering from diabetes mellitus (hereinafter referred to as "diabetes"), blood is often drawn many times a day.

Diabetes is a major health problem directly affecting over ten million people in the United States. The prevalence of the disease is increasing rapidly. Most people suffering from diabetes face the probability of major complications and shortened life spans. Diabetes is currently the seventh leading cause of death in the United States, and has been attributed to 35,000 to 50,000 deaths and costs of more than 20 billion dollars per year.

Diabetes is a disorder of carbohydrate metabolism characterized by elevated blood sugar (hyperglycemia), sugar in the urine (glycosuria), excessive urine production (polyuria), excessive thirst (polydipsia), and increase in food intake (polyphagia). Diabetes is a chronic, incurable disease, but symptoms can be ameliorated and life prolonged by proper therapy. Diabetes results from the inadequate production or utilization of insulin.

Insulin is a hormone secreted by the pancreas which is essential for the proper metabolism of blood sugar (glucose) and for the maintenance of the proper blood glucose level. Severe insulin deficiency, or less severe insulin deficiency coupled with other conditions, can cause ketoacidosis which may lead to coma and life-threatening crisis.

Chronic diabetes is associated with vascular and neurologic degeneration, and persons with diabetes are at increased risk of heart disease, blindness, renal failure, and inadequate circulation and sensation in peripheral tissues. Women with diabetes also have increased risk of stillbirths and congenital malformations in their children.

These direct consequences of diabetes make it a disease that is costly and difficult to manage. However, the complications of diabetes are caused primarily by elevated blood glucose levels, and these complications can be avoided in most cases by monitoring and control of blood glucose levels and close medical supervision with appropriate intervention. Thus, blood sugar determinations may need to be made at frequent intervals in order to know if, when, and how much insulin is needed to control blood glucose.

Attempts have been made to monitor blood glucose noninvasively. As used in this specification, the term "noninvasive blood glucose monitoring" means determining blood glucose concentration without actually drawing the patient's blood. For example, efforts to monitor blood glucose based upon glucose concentration in a patient's saliva or breath have failed. The reason for these failures is that there is no correlation between glucose in saliva or breath and the actual blood glucose levels. In fact, glucose does not naturally cross body membranes such as the buccal mucosa or membranes of the skin. Because most body membranes are naturally impermeable to glucose, the presence of glucose has historically been used to test whether tissue is intact in transdermal experiments.

In view of the foregoing, it will be appreciated that the development of apparatus and methods for noninvasive blood glucose monitoring would be a significant advancement in the art.

It would be another significant advancement in the art to provide apparatus and methods for noninvasive blood glucose monitoring which provide accurate and reproducible correlation with actual blood glucose levels.

Additionally, it would be a significant advancement in the art to provide apparatus and methods for noninvasive blood glucose monitoring which provide rapid results in sufficient time to administer appropriate medication.

Such apparatus and methods for noninvasive blood glucose monitoring are disclosed and claimed herein.

BRIEF SUMMARY AND OBJECTS OF THE INVENTION

The present invention is directed to novel methods and apparatus for noninvasive blood glucose monitoring. According to the present invention, blood glucose is monitored noninvasively by causing glucose to diffuse across epithelial membranes and then capturing and measuring that glucose for correlation to determine the blood glucose level. As used in this specification, the term epithelium or epithelial membrane refers to a variety of different dermal and mucosal surfaces.

In one preferred embodiment within the scope of the present invention, glucose diffuses across the buccal mucosal membrane into a glucose receiving medium. The glucose receiving medium includes a permeation enhancer capable of increasing the glucose permeability across the mucosal membrane. The glucose receiving medium is positioned against the mucosal membrane so that the permeation enhancer alters the permeability of the mucosal membrane which it contacts. After sufficient time delay, the glucose receiving medium is removed and analyzed for glucose concentration using conventional analytical techniques.

In another preferred embodiment within the scope of the present invention, glucose diffuses across the skin into a glucose receiving medium. As described above, the glucose receiving medium includes a permeation enhancer capable of increasing the glucose permeability across skin. The glucose receiving medium is positioned against the skin so that the permeation enhancer alters the permeability of the skin which it contacts. After a predetermined time, the glucose receiving medium is removed and analyzed for glucose concentration. The glucose receiving medium is capable of releasing a permeation enhancer and receiving glucose.

The driving force behind glucose diffusion from blood into the glucose receiving medium is the glucose concentration gradient. The glucose receiving medium preferably has a relatively low glucose concentration for the entire duration of the measurement, while the interstitial fluid, which is in equilibrium with the capillary blood vessels perfusing the buccal mucosa and dermis, has a substantially higher glucose concentration. By enhancing the glucose permeability of the mucosal membrane or dermis, a measurable amount of glucose diffuses into the glucose receiving medium.

The apparatus within the scope of the present invention includes means for supporting the glucose receiving medium. Such means for supporting the glucose receiving medium may include a housing which holds and contains the glucose receiving medium. The means for supporting the glucose receiving medium may also include a hydrogel.

The apparatus also includes means for temporarily positioning the glucose receiving medium against the mucosal membrane or skin. For example, if the apparatus includes a housing for supporting the glucose receiving medium, then an adhesive composition is preferably used to temporarily position the glucose receiving medium against the mucosal membrane. If the apparatus includes a hydrogel for supporting the glucose receiving medium, then the hydrogel itself may adhere directly to the mucosal membrane or skin.

In addition, other means for temporarily positioning the glucose receiving medium against the mucosal membrane may include a lollipop-like configuration wherein a stick or holder aids in properly positioning the device against the mucosal membrane. Alternatively, a bandage or wrap configuration may be used to temporarily position the glucose receiving medium against the skin.

An important feature within the scope of the present invention is the use of a rate limiting membrane or medium. It will be appreciated that the overall rate that glucose diffuses through the epithelial membrane into the glucose receiving medium depends upon the individual glucose permeabilities of the membranes or media that the glucose must pass through to enter the glucose receiving medium. The overall glucose diffusion rate is determined by the net resistance of all diffusional components, the net diffusion being dominated by the single diffusion component with the lowest glucose permeability. Thus, if a rate limiting membrane or medium having a precise and reproducible permeability is used, the overall glucose diffusion rate may be maintained relatively constant despite variations in epithelial membrane permeability from person to person, time to time, and even position to position.

It is, therefore, an object of the present invention to provide apparatus and methods for noninvasive blood glucose monitoring thereby avoiding the inconvenience and risk associated with traditional invasive blood glucose monitoring techniques.

An additional and necessary object of the present invention is to provide apparatus and methods for noninvasive blood glucose monitoring which provide accurate and reproducible correlation with actual blood glucose levels.

Another important object of the present invention is to provide apparatus and methods for noninvasive blood glucose monitoring which provide rapid results in sufficient time to administer appropriate medication.

Yet another important object of the present invention is to provide apparatus and methods for noninvasive blood glucose monitoring which provides accurate results from person to person.

These and other objects and features of the present invention will become more fully apparent from the following description and appended claims, taken in conjunction with the accompanying drawings, or may be learned from the practice of the invention.

DETAILED DESCRIPTION OF THE PREFERRED EMBODIMENTS

Figure 1:
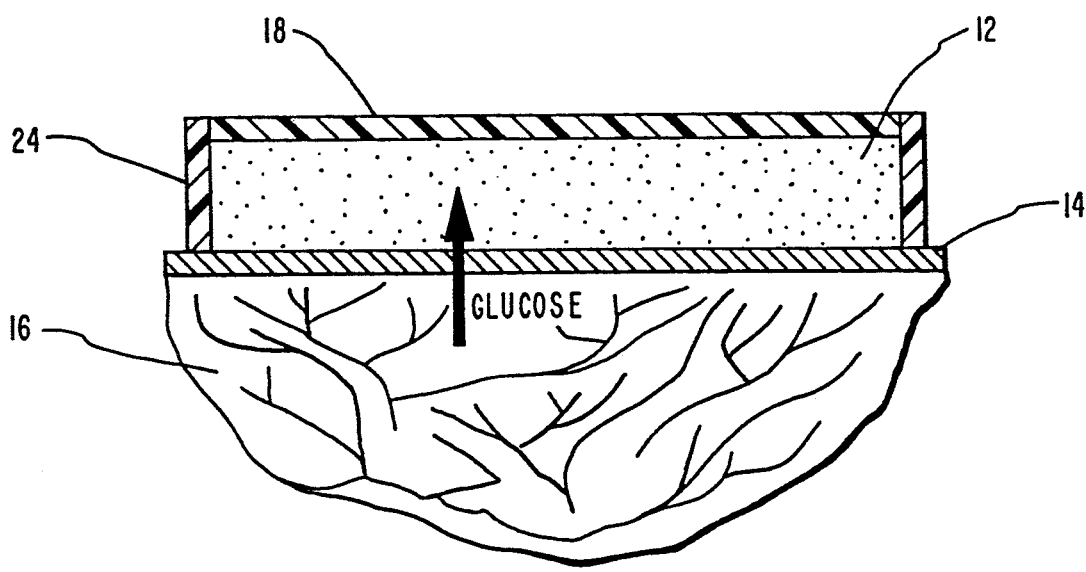
FIG. 1 is a cross-sectional schematic view of the noninvasive glucose monitoring process of the present invention.

The present invention is directed to novel methods and apparatus for noninvasive blood glucose monitoring. Such noninvasive techniques avoid the inconvenience and risks associated with traditional invasive glucose monitoring techniques because blood does not need to be drawn from a patient.

According to the present invention, blood glucose is monitored noninvasively by correlation with amount of glucose which permeates an epithelial membrane into a glucose receiving medium over a specified time period. As used in this specification, the term epithelium or epithelial membrane refers to both dermal and mucosal surfaces of the body. Epithelial membranes are generally impermeable to glucose; therefore, a glucose permeation enhancer capable of increasing the glucose permeability across the epithelial membranes is preferably included in the glucose receiving medium in order to enable glucose to back-diffuse from the interstitial fluid into the glucose receiving medium. Alternatively, it may be useful to pretreat the epithelial membrane with a permeation enhancer before applying the glucose receiving medium.

I. THEORETICAL CONSIDERATIONS

According to the apparatus and methods within the scope of the present invention, glucose diffuses from the interstitial fluid, which is in equilibrium with capillary blood vessels perfusing the epithelial membrane, across the membrane into a glucose receiving medium. From a theoretical viewpoint, the interstitial fluid in equilibrium with the capillary vessels is considered a donor chamber, and the glucose receiving solution is considered a receiver chamber. The donor chamber and the receiver chamber are separated by the epithelial membrane. In the donor chamber, there is a finite concentration ($C_o$) of permeant corresponding to glucose. The permeant concentration in the receiver chamber is zero at an initial time $t=0$.

If the concentration of the permeant in the donor chamber is kept constant ($C_o$) and the permeant concentration in the receiver chamber is much lower than $C_o$ for the entire experiment, then the amount of the permeant in the receiver chamber as a function of time is approximated by:

$$Q(t) = A \cdot C_o \left[ \frac{Dt}{h} - \frac{h}{6} - \frac{2h}{\pi^2} \sum_{n=1}^{\infty} \frac{(-1)^n}{n^2} e^{-n^2\pi^2 Dt/h^2} \right]$$

the diffusion lag time t(lag) is given by:

$$t(\text{lag}) = \frac{h^2}{6D}$$

and the flux of the permeant is given by:

$$\text{Flux} = \frac{1}{A} \cdot \frac{dQ(t)}{dt}$$

where "Q(t)" is the mass of the permeant in the receiver chamber at time "t", "D" is the diffusion coefficient of the permeant in the membrane, "h" is the thickness of the membrane, "t" is time, and "A" is the area of the membrane. See Flynn, et al., 63 *Journal of Pharmaceutical Sciences* 479 (1974).

From the foregoing equations both Q(t) and flux are proportional to $C_o$ at any time. Since both Q(t) and flux(t) are at all times proportional to the glucose concentration in the blood, $C_o$, they can be used to monitor the blood glucose concentration. However, in practice, precise measurement of Q(t) and the flux can only be made after t(lag) since Q(t) before t(lag) is very low.

Reference is now made to FIG. 1. The foregoing equations are valid in those situations where the permeability coefficient of glucose receiving medium 12 is substantially greater than that of epithelial membrane 14. In such cases, glucose receiving medium 12 acts as a glucose "sink." The quantity of glucose diffusing from interstitial fluid 16, through the epithelial membrane 14, and into glucose receiving medium 12, is determined by the most resistant layer along the diffusion pathway—epithelial membrane 14.

On the other hand, if the permeability coefficient of glucose receiving medium 12 is substantially less than that of epithelial membrane 14, than the quantity of glucose entering the glucose receiving medium is limited by glucose receiving medium 12.

Figure 2:
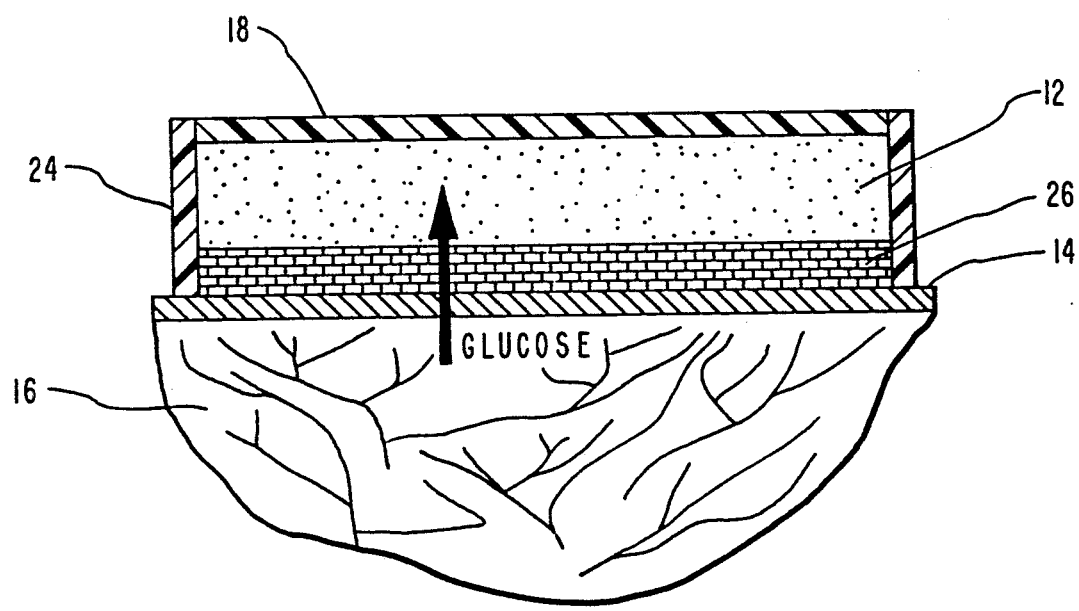
FIG. 2 is a cross-sectional schematic view of the noninvasive glucose monitoring process of the present invention using a rate regulating membrane.

Referring now to FIG. 2, one or more additional membranes 26 may be placed between the epithelial membrane and the glucose receiving medium to achieve a rate regulating function. In this case, it is preferred that the permeability coefficient of rate regulating membrane 26 is significantly lower than that of epithelial membrane 14 and that of glucose receiving medium 12. Thus, the quantity of glucose entering the glucose receiving medium is limited or regulated by the most resistant layer of the glucose diffusion pathway—membrane 26.

From a theoretical viewpoint, glucose must diffuse through two membranes to enter the glucose receiving medium: the epithelial membrane and the rate regulating membrane. The effective permeability coefficient of the combined membranes is given by:

$$P_T = P_M P_R / (P_M + P_R)$$

where "$P_T$", "$P_M$", and "$P_R$" are the permeability coefficients of the combined membrane, the epithelial membrane, and the rate regulating membrane, respectively. $P_R$ can be made precisely and reproducibly by modern techniques, while $P_M$ varies from person to person, time to time, and even position to position within the same type of epithelial membrane.

The above equation suggests that if $P_R$ is significantly lower than $P_M$, $P_T$ will stay relatively stable despite variations in $P_M$. For example, if $P_R = \frac{1}{5}P_M$, a 30% variation in $P_M$ will only cause about a 6% variation in $P_T$.

In a more sophisticated device within the scope of the present invention, a rate regulating medium or membrane is used. In the case of a rate regulating medium, the permeability coefficient of the glucose receiving medium is significantly lower than that of the epithelial membrane. In the case of the rate regulating membrane, one or several membranes are placed between the epithelial membrane and the glucose receiving membrane.

In both of the above cases the quantity of glucose permeated into the glucose receiving medium is given by $$Q(t) = C_o \cdot f(A, D_M, D_R, h_M, h_R, t)$$

where "$C_o$" is the concentration of the glucose in the interstitial fluid or capillary blood vessels; "A" is the area of contact; "$D_M$" and "$D_R$" are diffusion coefficients of glucose in the epithelial membrane and in the rate regulating membrane, respectively; "$h_M$" and "$h_R$" are the thicknesses of the epithelial membrane and the rate regulating membrane, respectively; "t" is the time passed from the beginning of contact; and "f" is a complicated function of the above variables. This equation is valid at all conditions, even if the "sink condition" is not maintained.

From the above equation, it is evident that the quantity of glucose permeated into the glucose receiving medium is proportional to the glucose concentration in the donor chamber (interstitial fluid and capillary blood vessels) at any time, provided that other variables in the above equation are kept relatively constant.

In a broad sense, the apparatus of the present invention is directed to a glucose receiving medium and to means for supporting the glucose receiving medium against an epithelial membrane. Permeation enhancers added to the glucose receiving medium alter the diffusion coefficient of glucose in the mucosal membrane thereby increasing Q(t) and flux and reducing t(lag). Without a permeation enhancer, the epithelial membrane is effectively impermeable to glucose. It has also been found that increasing the concentration or potency of the permeation enhancer significantly reduces the diffusion lag time. In fact, dramatically increasing the permeation enhancer concentration renders the lag time substantially negligible and enables rapid detection of the blood glucose level noninvasively.

II. PREFERRED APPARATUS OF THE PRESENT INVENTION

Figure 3:
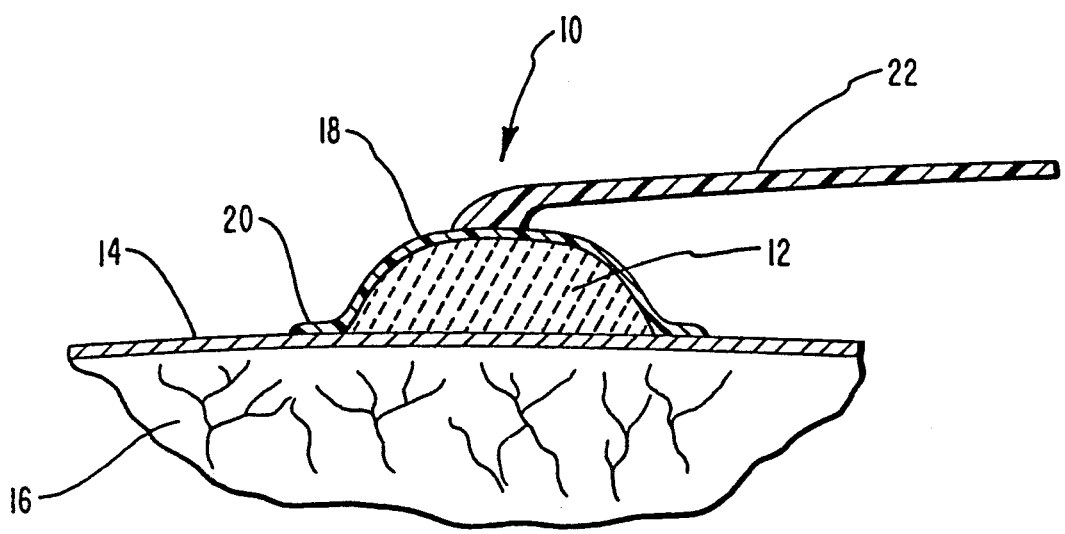
FIG. 3 is a cross-sectional view of one possible apparatus within the scope of the present invention.

Reference is made to FIG. 3 wherein one possible apparatus within the scope of the present invention is illustrated in a cross-sectional view. Noninvasive glucose monitoring device 10 includes glucose receiving medium 12. Glucose receiving medium 12 is positioned against epithelial membrane 14. Glucose receiving medium 12 includes a permeation enhancer (not shown) for improving the glucose permeability of epithelial membrane 14.

Glucose is preferably soluble in the glucose receiving medium. Hence, water is one currently preferred glucose receiving medium. Other compositions which dissolve glucose may also be suitably used as glucose receiving media within the scope of the present invention.

Suitable glucose receiving media should not unfavorably react with glucose or the permeation enhancer. The glucose receiving medium preferably does not interfere with glucose concentration measurements. It should also be nontoxic to the epithelial membrane and chemically and physically stable (e.g., does not degrade and nonvolatile).

It is also within the scope of the present invention to provide a glucose receiving medium containing a complexing agent which selectively combines with glucose to form an insoluble product. If such a complexing agent is included in the glucose receiving medium, then the resulting glucose complex is preferably detectable using known analytical techniques. The resulting insoluble glucose product may facilitate quantifying the glucose concentration. Lecithins and other sugar binding materials may be suitably used.

Typical permeation enhancers capable of improving the glucose permeability across the epithelial membrane include many natural bile salts such as sodium cholate, sodium glycocholate, sodium glycodeoxycholate, taurodeoxycholate, or sodium deoxycholate. Other permeation enhancers such as sodium lauryl sulfate, salts and other derivatives of saturated and unsaturated fatty acids, surfactants, bile salt analogs, derivatives of bile salts, or such synthetic permeation enhancers as described in U.S. Pat. No. 4,746,508 may also be used.

It has been found that the effectiveness of some enhancers varies depending on the type of epithelium. For example, some enhancers known to improve skin glucose permeability are not as effective when used to enhance mucosal membrane permeability. The following enhancers are particularly effective when used with the some mucosal membranes (nasal, rectal, gastrointestinal), but less effective when used with buccal mucosal membranes: IGEPAL 10.5 (octylphenoxy poly(ethoxyethanol) 10.5), EDTA (ethylenediaminetetraacetic acid), sodium oleate, and sodium taurocholate (a bile salt).

In addition, the effectiveness of some enhancers may vary depending on the chemical compound to be permeated. The following enhancers effectively alter epithelial permeability with respect to certain drugs, but are not very effective at promoting glucose permeability: ethanol, low chain alcohols, and solvent-type enhancers used transdermally.

The following enhancers have been found to be particularly effective at enhancing the transmucosal glucose permeability: sodium cholate, sodium dodecyl sulfate, sodium deoxycholate, and taurodeoxycholate. The following enhancers have been found to be particularly effective at enhancing the dermal glucose permeability individually or in combination: ethanol/water (with or without cell envelope disordering compounds), dimethyl sulfoxide (DMSO)/water, and isopropyl alcohol with methyl laurate (a cell envelope disordering compound).

The enhancer concentration within the receiving medium may be varied depending on the potency of the enhancer and the desired epithelial membrane. Other criteria for determining the enhancer concentration include the sensitivity of the glucose detection methods, the desired lag time. The upper limit for enhancer concentration is set by toxic effect to or irritation limits of the epithelial membrane. The solubility of the enhancer within the receiving medium may also limit enhancer concentration.

The following is a list of typical enhancers and an exemplary concentration range for each enhancer:

| Enhancer | Operational Concentration | Preferred Range |
|---|---|---|
| sodium cholate | 0.1%–50% | 1%–16% |
| sodium dodecyl sulfate | 0.01%–10% | 0.1%–2% |
| sodium deoxycholate | 0.1%–50% | 1%–16% |
| taurodeoxycholate | 0.1%–50% | 1%–16% |
| sodium glycocholate | 0.1%–50% | 1%–16% |
| sodium taurocholate | 0.1%–50% | 1%–16% |
| IGEPAL 10.5 | 0.05%–15% | 0.5%–5% |
| EDTA | 0.01%–5% | 0.1%–1% |
| sodium oleate | 0.1%–10% | 0.5%–5% |
| DMSO | 0.1%–99% | 5%–50% |
| Methyl Laurate in IPA* | 0.1%–20% | 0.5%–5% |
| Glyceryl Monooleate in IPA* | 0.1%–60% | 0.5%–5% |
| Ethanol | 5%–100% | 10%–50% |

*IPA = isopropyl alcohol

The driving force behind glucose diffusion into glucose receiving medium 12 is the glucose concentration gradient between the interstitial fluid 16 and receiving medium 12. The resistance to the permeation is determined by the permeability of epithelial membrane 14, the permeability of glucose receiving medium 12, or some other rate regulating membrane or media.

The glucose receiving medium preferably has a relatively low glucose concentration for the entire duration of measurement with respect to that in the interstitial fluid and capillary blood vessels, yet at the end of the measurement, the glucose concentration in the receiving medium is high enough to be measured precisely. By enhancing the glucose permeability of the epithelial membrane, a measurable amount of glucose diffuses into the glucose receiving medium.

The actual amount of glucose which diffuses into the glucose receiving medium depends upon many factors such as the type of epithelial membrane, the enhancer used, the enhancer concentration, the contact exposure time, the type of glucose receiving medium, the surface area in contact with the glucose receiving medium, intimacy of contact between the glucose receiving medium and the membrane, and the solubility of glucose in the glucose receiving medium. It is within the skill in the art to modify the foregoing factors in order to cause the desired amount of glucose to diffuse into the glucose receiving medium.

The amount of glucose which must diffuse into the glucose receiving medium in order to be accurately measured depends upon the sensitivity of the analytical glucose detection methods used. Currently, techniques which detect glucose having a concentration as low 0.5 μg/ml provide suitable results for the diagnostic methods within the scope of the present invention. Other criteria useful in selecting a suitable glucose detection method include the glucose specificity and convenience of the method.

A housing 18 encloses the glucose receiving medium and protects the glucose receiving medium from potential glucose contamination sources such as saliva. Hence, one important function of housing 18 is to isolate the glucose receiving medium from glucose contamination sources. Another important function of housing 18 is to provide support for the glucose receiving medium. Housing 18 is preferably constructed of a material which is nontoxic, chemically stable, nonreactive with glucose and the permeation enhancers used, and inexpensive. Suitable materials include: polyethylene, polyolefins, polyamides, polycarbonates, vinyl polymers, and other similar materials known in the art.

Housing 18 may take many different shapes; however, the housing should define a chamber for holding a quantity of glucose receiving medium and provide an opening such that the glucose receiving medium may be placed directly against the epithelial membrane. Housing 18 may also include flanges 20 located about the periphery of the housing for receiving an adhesive so that the housing may be maintained in position against epithelial membrane 14. Housing 18 may also include an access port (not shown) through which glucose receiving medium may be introduced into the housing or through which the glucose receiving medium may be directly tested for glucose or removed for external testing while the housing is maintained in position against the epithelial membrane.

When housing 18 is to be used for measuring glucose diffusion across a mucosal membrane, such as those in the mouth, a handle 22 may optionally be attached to housing 18 to facilitate placement and removal of the apparatus. Handle 22 is particularly desirable to provide user-control of placement and removal and to maintain housing 18 in contact with the mucosal tissues.

It should be noted that the apparatus within the scope of the present invention does not require a housing as illustrated in FIG. 3. Other means for supporting and positioning glucose receiving medium 12 against epithelial membrane 14 may be used. For example, it has been found that hydrogels not only provide suitable support for the glucose receiving medium, but also adhere to epithelial membranes, particularly mucosal membranes.

When a hydrogel is used to support the glucose receiving medium, the bioadhesive hydrogel itself may be used to temporarily position the glucose receiving medium against the epithelial or mucosal membrane. In the context of a hydrogel, the glucose receiving medium corresponds to the aqueous portion of the hydrogel, whereas the cellulose frame or other material forming the hydrogel provides the necessary support of the glucose receiving medium. Hence, the glucose receiving medium within the scope of the present invention may be supported in a hydrogel.

Importantly, many hydrogels are inherently sticky. Such bioadhesive hydrogels adhere directly to mucosal tissues. Cellulose, including hydroxypropylcellulose and other cellulose derivatives known in the art, carbopol, gelatin, and other known substance which produce hydrogels may be used within the scope of the present invention.

Other support substances which perform substantially the same function as hydrogels may also be used. For example, creams, emulsions, suspensions, and other solid and semisolid media may also provide suitable support for a glucose receiving medium. However, glucose may not be as soluble in a nonaqueous glucose receiving medium incorporated into such media. A sponge-like embodiment may also provide suitable support for a glucose receiving medium.

Whether a hydrogel or other substance is used to support a glucose receiving medium, it is important that the glucose receiving medium be safely supported and maintained in contact with the epithelial tissues for sufficient time to effect glucose diffusion across the epithelial membrane.

In some embodiments within the scope of the present invention, the hydrogel or other support substance may be preferably covered or sealed from potential contaminants such as saliva. A nonpermeable membrane, such as a thin plastic layer, would protect the hydrogel from potential contamination. A housing, as described above, would also suitably protect the hydrogel. In addition, a housing (and optionally a handle) would facilitate positioning and removal of the hydrogel.

Depending on the thickness and total surface area of the hydrogel or other support substances, the edges may not need to be covered or sealed. In this regard, lateral edges 24, illustrated in FIGS. 1 and 2, may not be necessary. Of course, if there is a significant risk of glucose contamination from saliva or foods, then it would be important to include lateral edges 24.

It will be appreciated that there are many other possible embodiments within the scope of the present invention which perform substantially the same function as the embodiment illustrated in FIG. 3. For example, clamps, buccal tapes, matrix patch type designs, and designs similar to the transdermal or transmucosal patches described in the patent literature may be used within the scope of the present invention.

III. USE OF THE PRESENT INVENTION

In use, the glucose receiving medium is preferably positioned directly against the epithelial membrane so that the permeation enhancer contacts the epithelial membrane and increases the glucose permeability of the membrane. Various epithelial membranes, including mucosal and dermal surfaces of the body, may be utilized within the scope of the present invention.

Some epithelial membrane surfaces are more preferable than others. For example, post auricular skin is preferable over the palm of the hand. The selection of a suitable epithelial membrane depends upon a number criteria, such as glucose permeability for a given quantity of enhancer, degree of irritation caused by the enhancer, lag time, convenience (e.g., buccal membrane is more accessible than nasal and rectal membranes), and the degree of vascularization.

After sufficient time delay, the glucose receiving medium is removed and analyzed for the presence of glucose using conventional analytical techniques. Variables affecting sufficient exposure time include: glucose detecting sensitivity, permeability, lag time, enhancer concentration, glucose receiving medium surface contact area to volume ratio, and temperature.

There are many different techniques known in the art for determining glucose concentration. For those experiments using transmucosal glucose detection methods, the glucose which diffused across the mucosal membrane was measured using a standard Glucose Diagnostic Kit Solution obtained from Sigma Chemical Co. (cat. #315-100). The procedure was modified slightly by using a glucose sample solution instead of blood. Glucose concentration as low as 0.5 $\mu$g/ml was accurately detected using this technique. In the transdermal glucose detection experiments, the glucose which diffused across the skin was measured using reverse-phase high pressure liquid chromatography ("HPLC"). Glucose concentration as low as 60 $\mu$g/ml was accurately detected using HPLC.

Because the glucose concentration within the glucose receiving medium is proportional to the patient's actual blood glucose level, once the glucose within the glucose receiving medium is determined the actual blood glucose level may be quickly calculated.

For user convenience, it may be desirable to incorporate a color indicator into the glucose receiving medium. In this way, the glucose concentration may be quickly determined by comparing any color change (not necessarily in the visible light spectrum) of the glucose receiving medium against a standard color chart. Examples of commercially available indicators include a combination of glucose oxidase, 4-aminoantipyrine, and p-hydroxybenzenesulfonate.

IV. EXAMPLES

The use of the methods for noninvasively monitoring blood glucose concentration within the scope of the present invention will be further clarified by a consideration of the following examples, which are intended to be purely exemplary of the use of the invention and should not be viewed as a limitation on any claimed embodiment.

EXAMPLE 1

In this example, blood glucose was monitored noninvasively in a laboratory dog. A 0.5 mm–1.0 mm thick layer of silicone grease was spread on the base of a diffusion cell to provide the adhesiveness and prevent leakage of the glucose receiving solution in the cell. The diffusion cell had an open bottom designed to be placed on the dog's buccal mucosa and an open top through which glucose receiving solution was added and removed. The area of the cell's open bottom was 1.89 cm$^2$. The diffusion cell was placed on the dog's buccal mucosa.

At time t=0, 2 ml of a glucose receiving solution were pipetted into the cell through the cell's open top. The glucose receiving solution was a 2% by weight solution of sodium cholate in deionized (DI) water. The glucose receiving solution was in direct contact with the buccal mucosa through the open bottom end of the diffusion cell.

One (1) ml of solution was withdrawn from the cell after 3 minutes. One (1) ml of fresh glucose receiving solution was pipetted into the cell immediately after sampling to maintain the volume of the solution in the cell at 2 ml. Sampling was repeated at time t=10 minutes and at 10 minute intervals thereafter up to 120 minutes. The dilution due to the replacement with the fresh glucose receiving solution was corrected for in the calculation of total amount of glucose permeated.

Each 1 ml sample from the diffusion cell was placed in a glass vial containing 2 ml of a standard Glucose Diagnostic Kit Solution (Sigma Chemical Co., cat. #315-100). The resultant 3 ml solution was incubated at room temperature for exactly 18 minutes. After incubation, the 3 ml solution was placed in a 1 cm path length cuvette cell. The absorbance of the mixture at 505 nanometers was measured by a colorimeter (Milton Roy, Spectronic 21).

Figure 4:
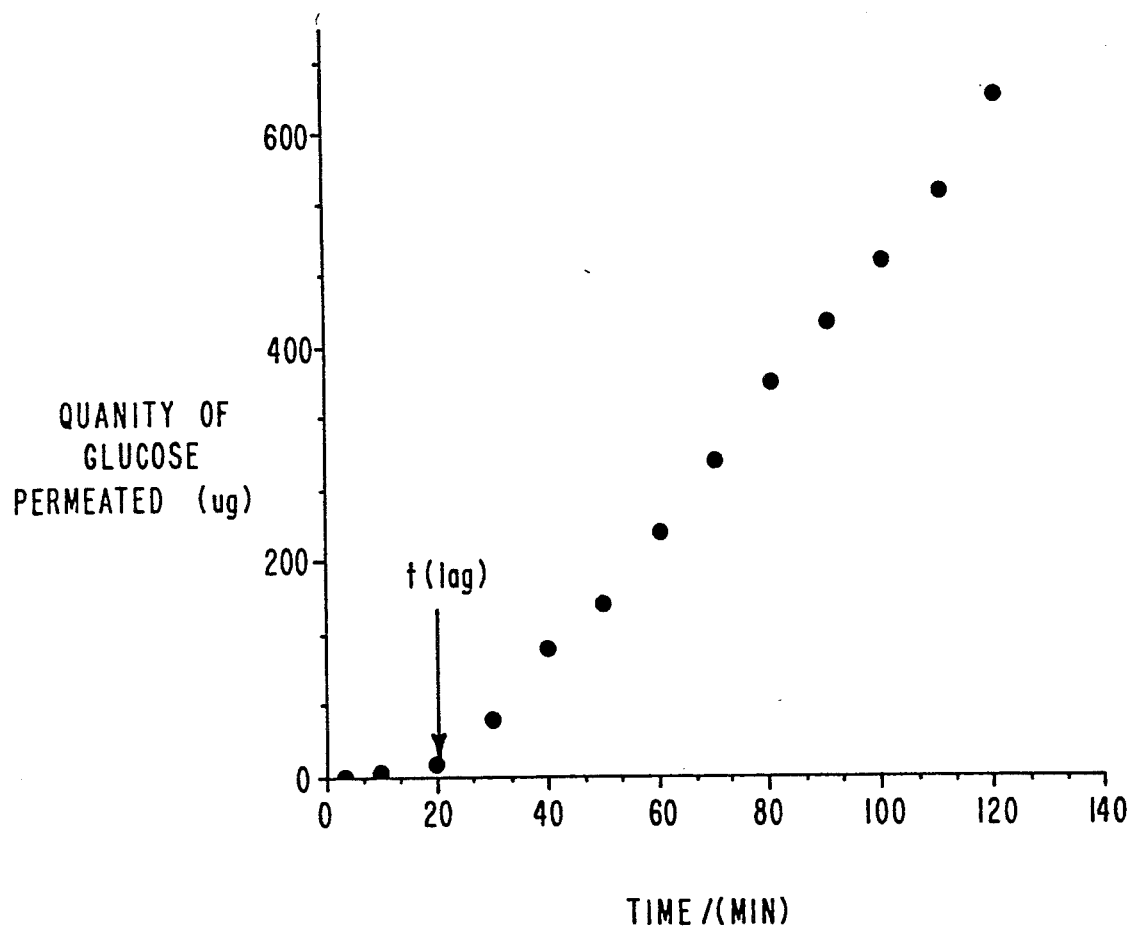
FIG. 4 is a graph of glucose permeated ($\mu$g) verses time for the results of Example 1.

The relationship between the glucose concentration in the sample and the absorbance is given by the following equation:

$$C\ (\mu g/ml) = A + B \times Absorbance$$

where A and B are constants determined by testing standard glucose concentration solutions. The glucose concentration in each sample, and from which the total amount of glucose permeated across the buccal mucosa at a given time, can thus be obtained. The experimental results of Example 1 are given in Table I and shown graphically in FIG. 4.

TABLE I

| n | t/min | absorbance | C in sample ($\mu$g/mL) | Glucose permeated ($\mu$g) |
|---|-------|-----------|-------------------------|----------------------------|
| 1 | 3.00 | 0.103 | 0.17 | 0.34 |
| 2 | 10.00 | 0.112 | 1.38 | 2.93 |
| 3 | 20.00 | 0.142 | 5.15 | 11.85 |
| 4 | 30.00 | 0.278 | 23.71 | 54.12 |
| 5 | 40.00 | 0.430 | 44.16 | 118.73 |
| 6 | 50.00 | 0.418 | 42.55 | 159.67 |
| 7 | 60.00 | 0.513 | 55.33 | 227.78 |
| 8 | 70.00 | 0.558 | 61.38 | 295.21 |
| 9 | 80.00 | 0.600 | 67.03 | 367.89 |
| 10 | 90.00 | 0.565 | 62.32 | 425.50 |
| 11 | 100.00 | 0.544 | 59.50 | 482.18 |
| 12 | 110.00 | 0.570 | 63.00 | 548.68 |
| 13 | 120.00 | 0.670 | 76.45 | 638.58 |

The total amount of glucose permeated is given by the following formula:

$$G_n = C_n \cdot V_{receiver} + \left(\sum_{i=1}^{n-1} C_i\right) \cdot V_{sample}$$

where "$G_n$" is total amount of glucose permeated ($\mu$g) through sample number n and "$C_n$" is the glucose concentration ($\mu$g/ml) in sample n ($C_n$=0 when n=0), "$V_{receiver}$" is the volume of receiver chamber fluid (2 ml), and "$V_{sample}$" is the volume of sample withdrawn from the cell (1 ml).

The actual blood glucose level was monitored by taking blood samples from the femoral artery about every 10 to 15 minutes for the whole duration of the procedure. The glucose concentration in the blood samples were determined by the combination of Glucostix (Ames 2628C) and Glucometer (type II, model 5625, Ames Division, Miles Labs, Inc., P.O. Box 70, Elkhart, Ind. 46515). The standard procedure as described in the user's manual of the Glucometer was followed.

EXAMPLE 2

Blood glucose was monitored noninvasively in a laboratory dog according to the procedure of Example 1, except that the blood glucose was artificially elevated. The elevation of the dog's blood glucose concentration was achieved by intravenous infusion of a glucose solution. The infusion rate was adjusted for the individual dog to achieve the desired blood glucose level.

With the particular dog used in this example, 6 grams/hour glucose was needed to increase the blood glucose level from about 97 mg/dl to about 211 mg/dl. It required about 2 hours to establish an elevated steady state blood glucose level. The experimental results of Example 2, along with that of Example 3, are shown graphically in FIG. 5.

The results of this example demonstrate that the glucose back diffusion flux, as well as the amount of glucose permeated, do reflect the actual blood glucose level change.

EXAMPLE 3

Blood glucose was monitored noninvasively in a laboratory dog according to the procedure of Example 1, except that the blood glucose was artificially suppressed. The same laboratory dog used in Example 2 was used in this Example. The suppression of the dog's blood glucose concentration was achieved by intravenous infusion of an insulin solution. The infusion rate was adjusted for the individual dog to achieve the desired blood glucose level.

With the particular dog used in this example, 0.9 U/hour insulin was needed to reduce the blood glucose level from about 97 mg/dl to about 34 mg/dl. It required about 2 hours to establish a suppressed steady state blood glucose level. Additional adjustment of the insulin infusion rate was necessary to maintain the glucose level relatively constant. The experimental results of Example 3, along with that of Example 2, are shown graphically in FIG. 5.

The results of this example demonstrate that the glucose back diffusion flux, as well as the amount of glucose permeated, do reflect the actual blood glucose level change.

Figure 5:
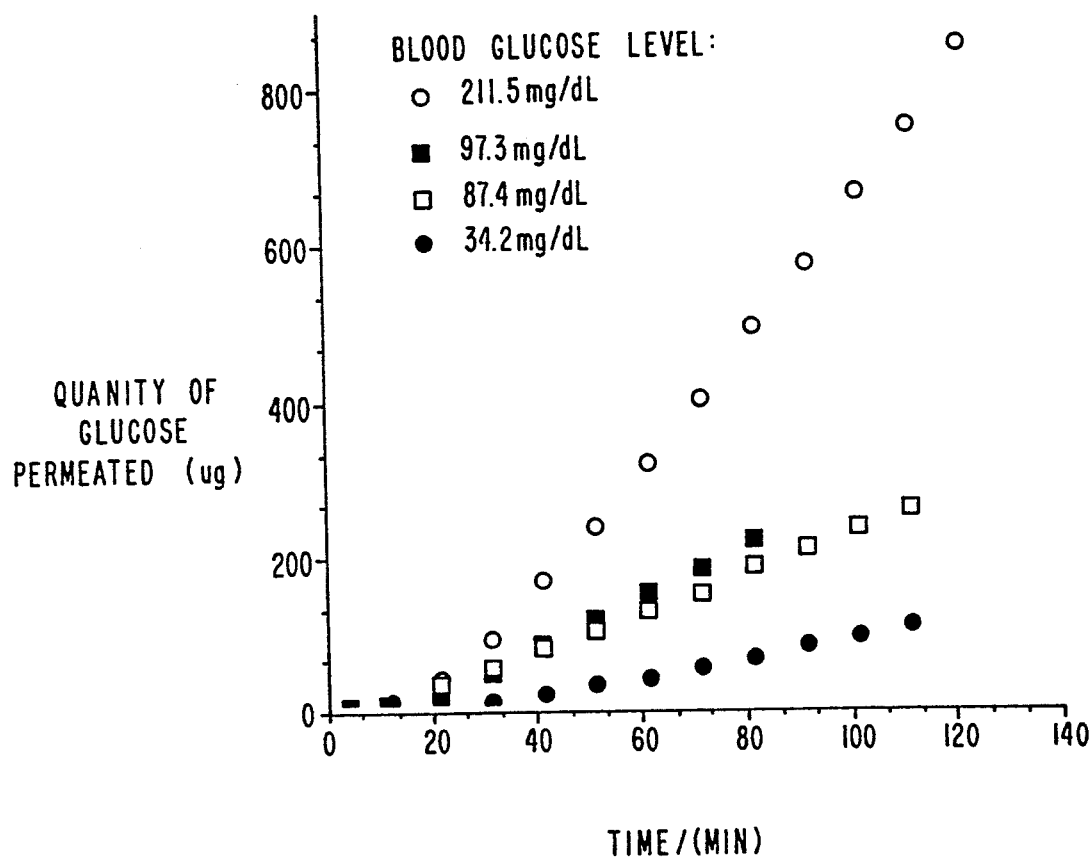
FIG. 5 is a graph of glucose permeated ($\mu$g/cm$^2$) verses time for the results of Examples 2 and 3.
Figure 6:
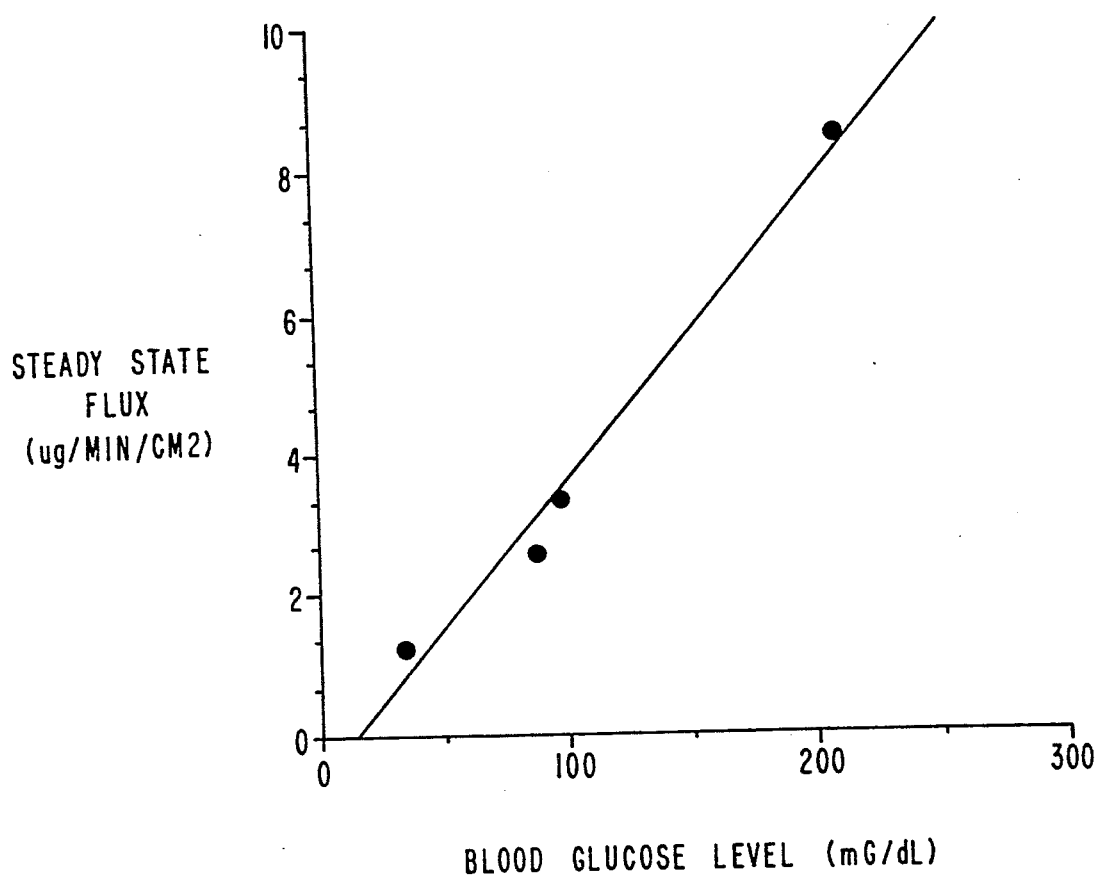
FIG. 6 is a graph of glucose flux ($\mu$g/min/cm$^2$) verses blood glucose level (mg/dl).

The glucose back diffusion flux of Examples 2 and 3 may be determined from the slope of the data plotted in FIG. 5. The glucose flux ($\mu$g/min/cm$^2$) was calculated and plotted in FIG. 6. The results of FIG. 6 demonstrate that glucose flux is proportional to the blood glucose level. Thus, by determining glucose flux it is possible to determine actual blood glucose levels.

EXAMPLE 4

Figure 7:
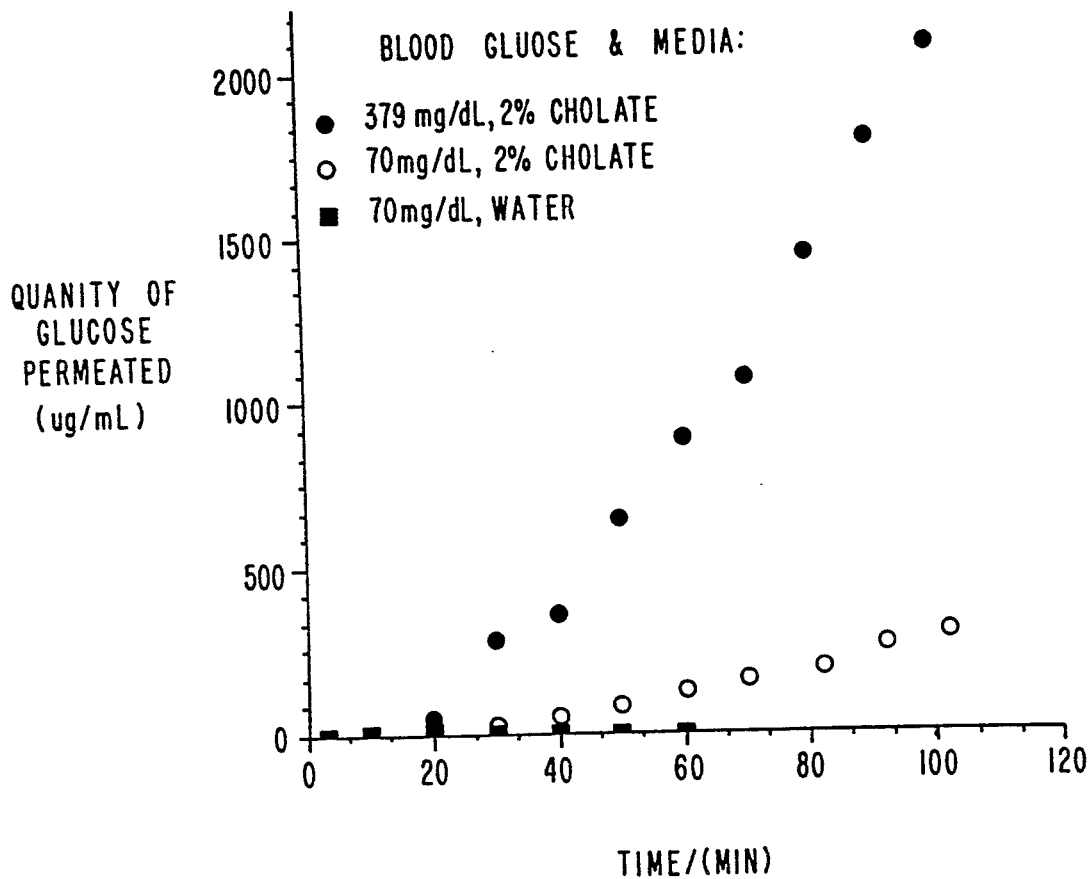
FIG. 7 is a graph of glucose permeated ($\mu$g) verses time for the results of Example 4.

Blood glucose was monitored noninvasively in a laboratory dog according to the procedure of Examples 1 and 2, except that a glucose receiving solution without a permeation enhancer was tested in addition to the glucose receiving solutions having 2% sodium cholate. The experimental results of Example 4 are shown graphically in FIG. 7. These results indicate that no glucose permeated the buccal mucosa without a permeation enhancer.

EXAMPLE 5

Blood glucose was monitored noninvasively in a laboratory dog according to the procedure of Example 1, except that the glucose receiving solution was a 2% by weight solution of sodium cholate in 30% ethanol and 70% deionized (DI) water.

Figure 8:
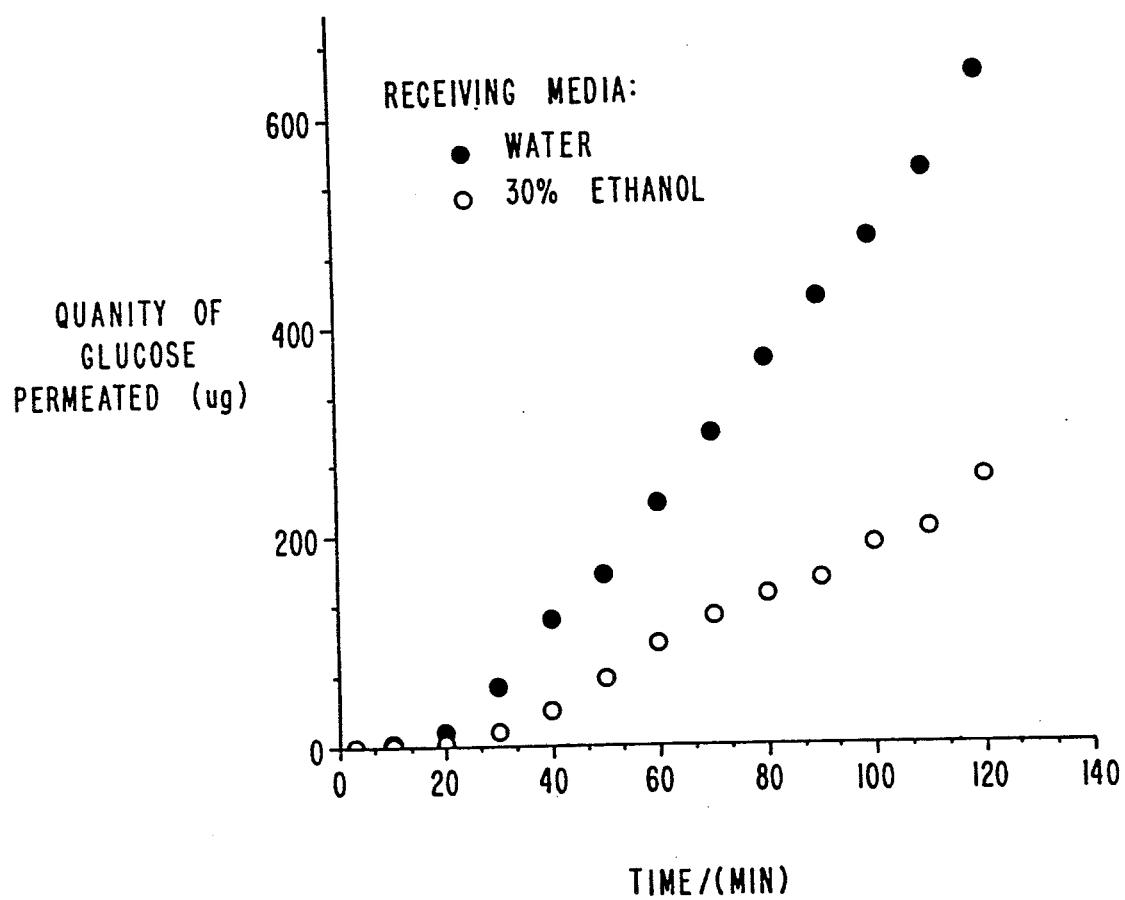
FIG. 8 is a graph of glucose permeated ($\mu$g) verses time for the results of Example 5.

The experimental results of Example 5 compared with results using the procedure of Example 1 are shown graphically in FIG. 8. These results indicate that the amount of glucose permeated when 30% ethanol is present in the glucose receiving solution is substantially lower than when no ethanol is present. It is currently believed that this result is due to the fact that the solubility of glucose in water is higher than the solubility in ethanol. Consequently, the tendency of glucose to permeate from plasma into the 30% ethanol solution is lower than into a deionized water solution.

EXAMPLE 6

Figure 9:
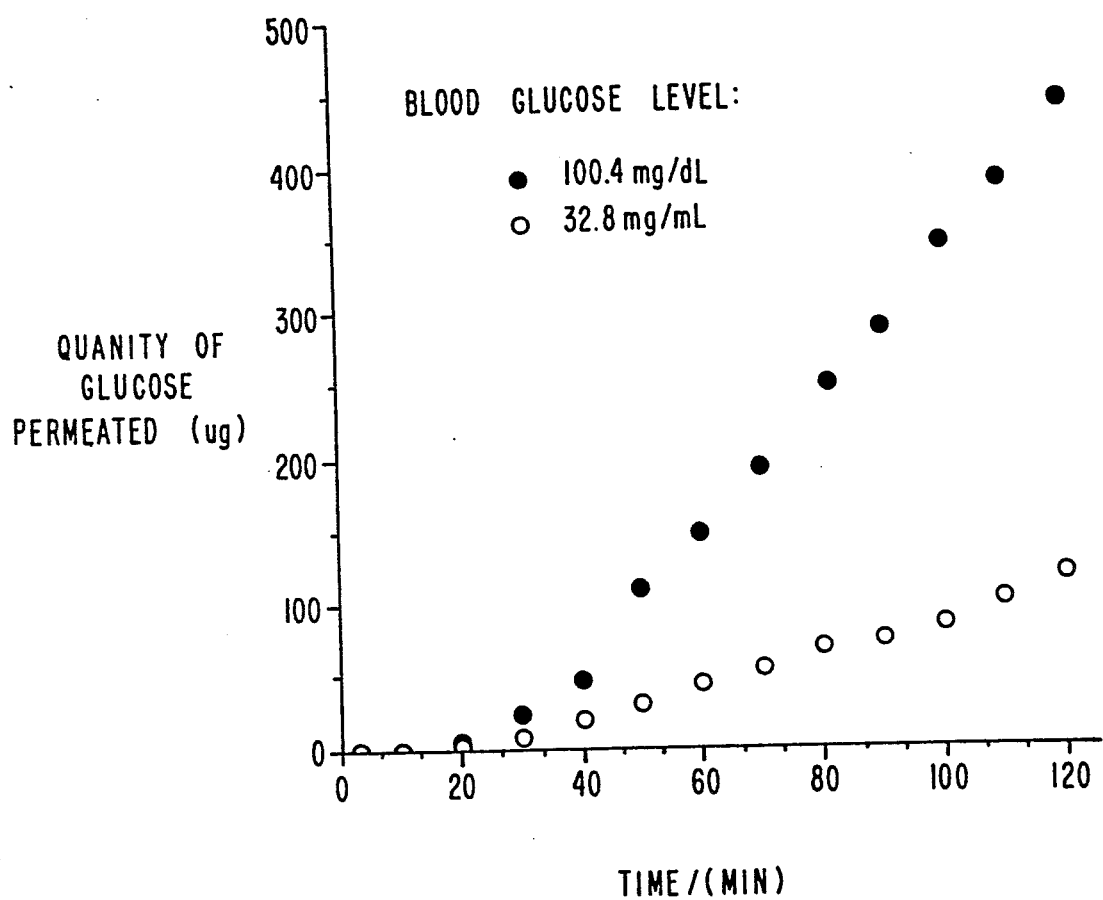
FIG. 9 is a graph of glucose permeated ($\mu$g) verses time for the results of Example 6.

Blood glucose was monitored noninvasively in a laboratory dog according to the procedure of Examples 1 and 3, except that the normal blood glucose level was about 100.4 mg/dl and that the suppressed blood glucose level was maintained about 32.8 mg/dl. The experimental results of Example 6 comparing the amount of glucose permeated ($\mu$g) over time when the blood glucose is suppressed and when the blood glucose is normal are shown graphically in FIG. 9. This example confirms that the blood glucose level changes may be monitored by the methods of the present invention.

EXAMPLES 7-17

In this example, blood glucose was monitored noninvasively in a laboratory dog according to the procedure of Example 1, except that a variety of different permeation enhancers were examined to determine their respective mucosal glucose permeability enhancement ability. The permeation enhancers tested in this example were sodium cholate, sodium dodecyl sulfate, sodium deoxycholate, taurodeoxycholate, sodium glycocholate, IGEPAL 10.5, EDTA, sodium oleate, and sodium taurocholate.

A glucose receiving medium was prepared for each respective permeation enhancer wherein the permeation enhancer concentration was 2% by weight in deionized water, except for EDTA which was tested at a concentration of 0.2% and 1%. Sodium oleate was also tested at an 8% concentration. Table II summarizes the experimental results. Those enhancers which were classified "good" resulted in diffusion of readily detectable quantities of glucose across the mucosal membrane. Those enhancers which were classified "poor" enabled barely detectable quantities of glucose to permeate the mucosal membrane. Enhancers classified "bad" did not enable detectable quantities of glucose to permeate the mucosal membrane.

TABLE II

| Example | Enhancer | Concentration | Results |
|---|---|---|---|
| 7 | sodium cholate | 2% | good |
| 8 | sodium dodecyl sulfate | 2% | good |
| 9 | sodium deoxycholate | 2% | good |
| 10 | taurodeoxycholate | 2% | good |
| 11 | sodium glycocholate | 2% | poor |
| 12 | sodium taurocholate | 2% | poor |
| 13 | IGEPAL 10.5 | 2% | bad |
| 14 | EDTA | 0.2% | bad |
| 15 | EDTA | 1% | bad |
| 16 | sodium oleate | 2% | bad |
| 17 | sodium oleate | 8% | bad |

EXAMPLE 18

In this example, blood glucose was monitored noninvasively in a laboratory dog using a hydrogel. The hydrogel was prepared by placing 2 g of hydroxypropylcellulose in a glass vial. The glass vial was positioned in a 55° C. water bath until temperature equilibrium was reached. Five (5) ml of 55° C. deionized water was then introduced into the vial. The mixture was stirred thoroughly and a slurry was formed. Hydroxypropylcellulose is insoluble in water 45° C. or warmer. Five (5) ml of room temperature deionized water containing 16% by weight sodium cholate was introduced into the vial. The mixture was stirred gently until a hydrogel was formed. The hydrogel was centrifuged for 45 minutes to remove any air bubbles. The resulting hydrogel had an 83% water content which contained 8% sodium cholate. The hydrogel was transparent and homogeneous.

Four slices of the hydrogel having a surface area of 1.04 cm$^2$ were placed on the buccal mucosa of a laboratory dog. Thirty (30) minutes later, two hydrogel slices were removed from the dog. Sixty (60) minutes later the remaining two hydrogel slices were removed. The actual blood glucose concentration for the dog was monitored during the experiment as described in Example 1. The average blood glucose concentration during the measurements was found to be about 100 mg/dl.

The hydrogel slices removed from the dog's buccal mucosa were weighed and placed in separate glass vials. Deionized water was added to the vials such that the combined weight of the hydrogel and the deionized water was 2.5 g. The vials were shaken until the hydrogel was swollen to at least double its original volume and a considerable part of the hydrogel was dissolved in the deionized water. The vials were shook for about 60 minutes. It was assumed that after 60 minutes of shaking, the glucose concentration in the gel and in the liquid are equal. This assumption has been confirmed experimentally.

One (1) ml of the solution was withdrawn from the vial and incubated with 2 ml glucose oxidase solution (Sigma, Glucose diagnostic Kit #315-100) for exactly 18 minutes. The absorbance of the mixture at 505 nanometers was measured by a colorimeter. The glucose concentration in the mixture, and from which the total amount of glucose in the hydrogel, was obtaining by using a calibration curve.

The calibration curve was prepared by placing five glucose solutions having glucose concentrations of C=0, 25, 50, 75, and 100 $\mu$g/ml respectively, into five glass vials. 2 ml of the standard glucose solution were placed in the respective vial. Each glass vial contained 0.4 g of hydrogel described above and 0.1 g deionized water. The vials were shaken for 60 minutes. Assuming the glucose concentrations in the gel and the liquid reached equilibrium by the end of the shaking, the liquid part of each vial had glucose concentrations of C=0, 20, 40, 60, and 80 $\mu$g/ml, respectively. The weight of the hydroxypropylcellulose (0.067 g) was ignored. One (1) ml of the liquid from each vial was incubated with 2 ml glucose oxidase solution for exactly 18 minutes, and the absorbance at 505 nanometers was measured. The absorbance verses glucose concentration relation was found to be:

$$C(\mu g/ml) = -14.82 + 130.45 \times \text{Absorbance}, R = 1$$

Because this relation is very close to that in water, it is believed the glucose concentration equilibrium between the hydrogel part and the liquid part was reached after 60 minutes of shaking.

Figure 10:
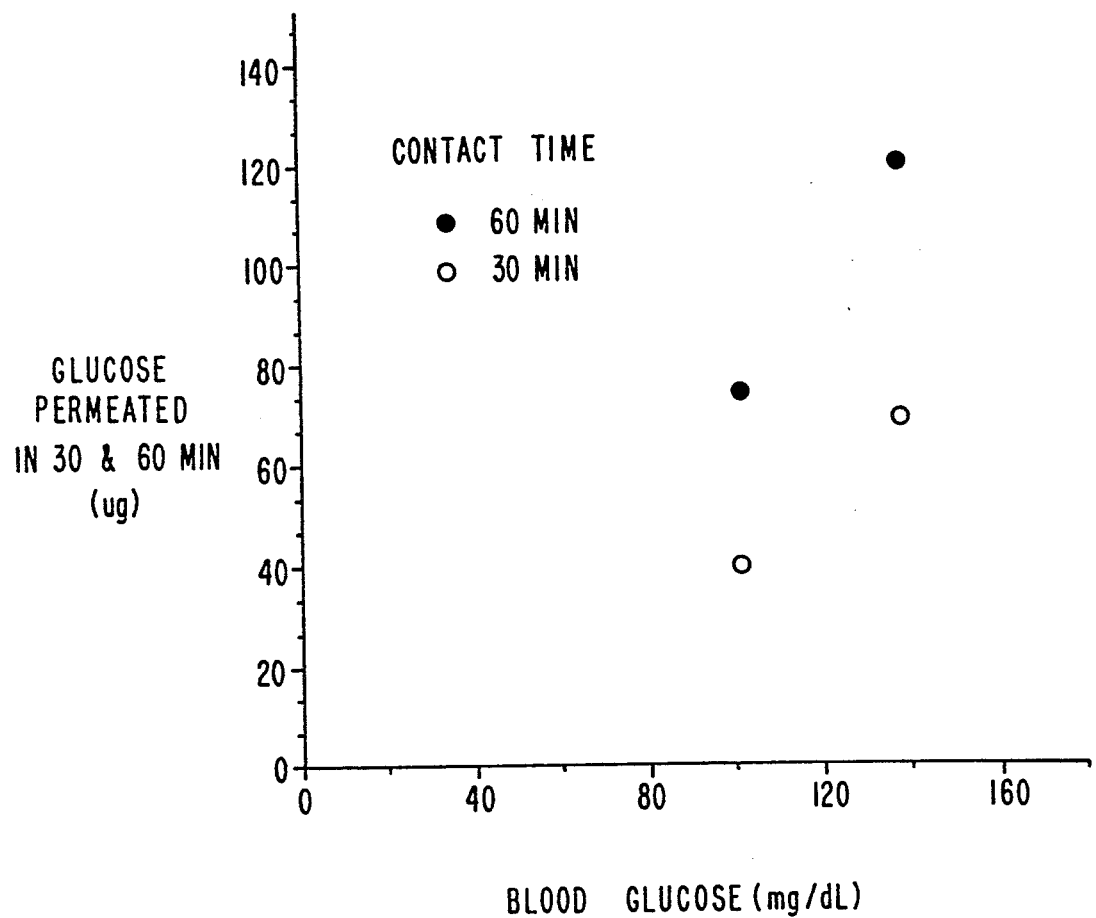
FIG. 10 is a graph of glucose permeated ($\mu$g/cm$^2$) verses blood glucose (mg/dl) for the results of Examples 18 and 19.

The total amount of glucose permeated into the hydrogel is shown in FIG. 10 as a function of blood glucose concentration. These results indicate that the amount of glucose in the hydrogel remarkably reflects the change in the blood glucose concentration. The relationship between the glucose in the hydrogel and the blood glucose level were remarkably linear. Considering the uncertainty in the blood glucose level measurements by the Glucostix - Glucometer and the intrinsic blood glucose level fluctuation at both natural level and the manipulated (elevated or suppressed) level, it can be concluded that the deviation from the linearity is within the experimental uncertainty and the fluctuation of the blood glucose level in the dog.

EXAMPLE 19

Blood glucose was monitored noninvasively in a laboratory dog using a hydrogel according to the procedure of Example 18, except that the blood glucose level was about 140 mg/dl. The same laboratory dog used in Example 18 was used in Example 19. The total amount of glucose permeated into the hydrogel is also shown in FIG. 10 as a function of blood glucose concentration.

EXAMPLE 20

Figure 11:
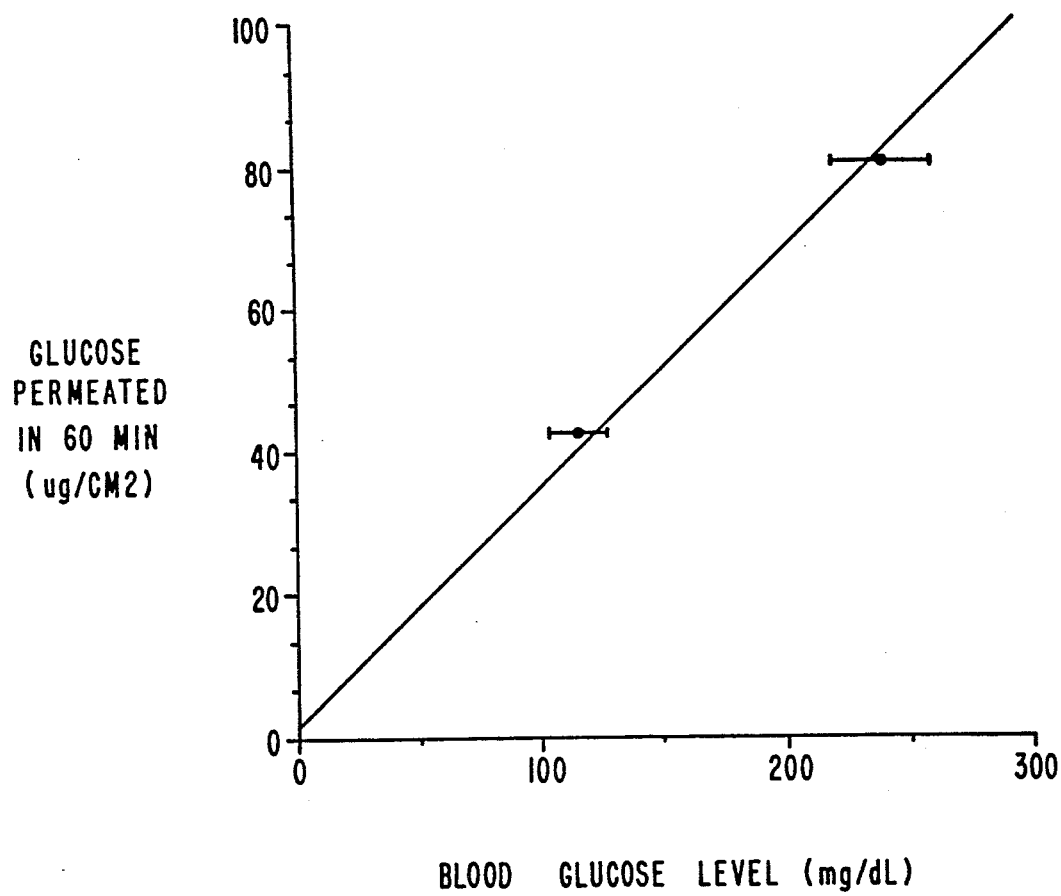
FIG. 11 is a graph of glucose permeated ($\mu$g/cm$^2$) verses blood glucose (mg/dl) for the results of Example 20.

Blood glucose was monitored noninvasively in a laboratory dog using a hydrogel according to the procedure of Example 18, except that the blood glucose level in the dog was elevated to about 245 mg/dl using the procedure described in Example 2. Blood glucose was also monitored in the same laboratory dog according to the procedure of Example 18, except that the normal blood glucose level was about 120 mg/dl. In both the normal and elevated blood glucose tests, the concentration of sodium cholate in the hydrogel was 4% by weight. In addition, the hydrogel was placed on the buccal mucosa only for a period of 60 minutes. The total amount of glucose permeated into the hydrogel, normalized to $\mu$g/cm$^2$, is shown in FIG. 11 as a function of blood glucose concentration (mg/dl).

EXAMPLE 21

Figure 12:
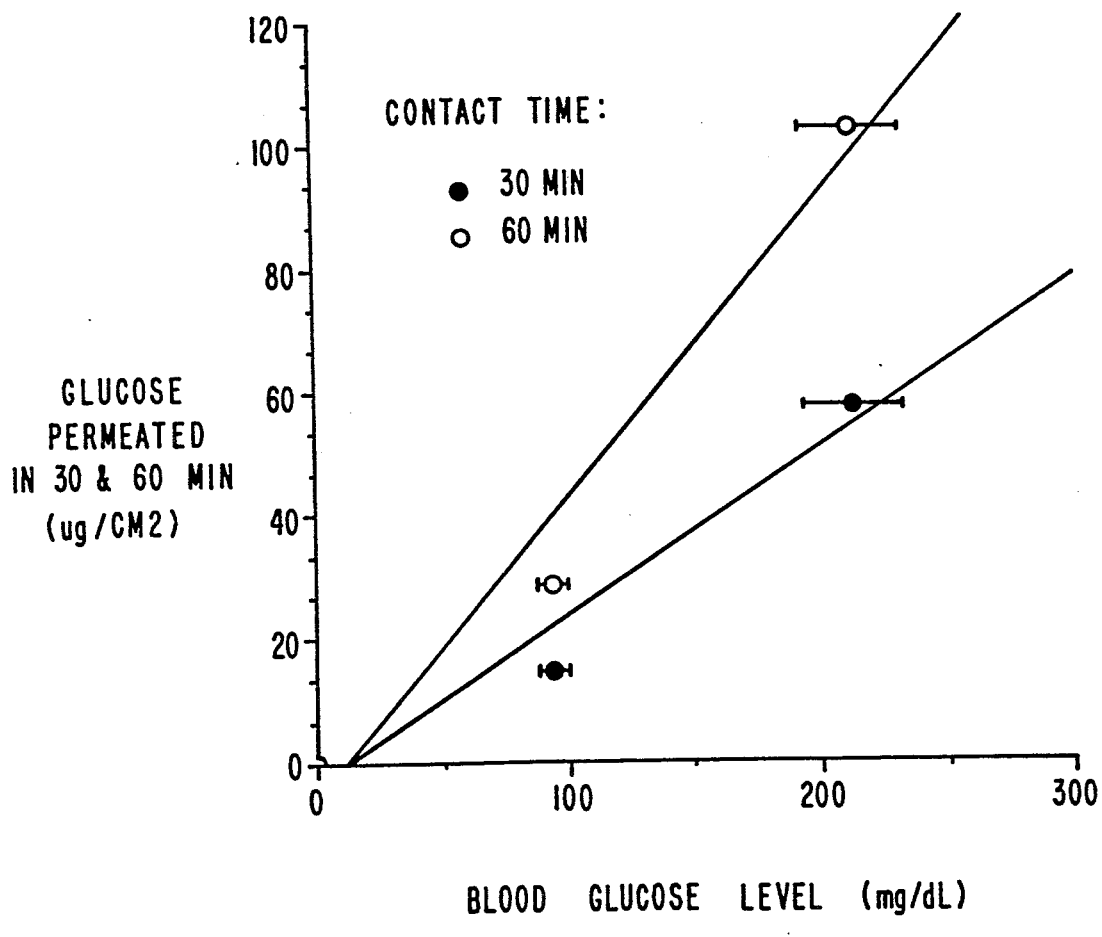
FIG. 12 is a graph of glucose permeated ($\mu$g/cm$^2$) verses blood glucose (mg/dl) for the results of Example 21.

Blood glucose was monitored noninvasively in a laboratory dog using a hydrogel according to the procedure of Example 18, except that the blood glucose level in the dog was elevated to about 210 mg/dl using the procedure described in Example 2. Blood glucose was also monitored noninvasively in the same laboratory dog using a hydrogel according to the procedure of Example 18, except that the normal blood glucose level was about 95 mg/dl. The total amount of glucose permeated into the hydrogel, normalized to $\mu$g/cm$^2$, for both the elevated and normal blood glucose levels is shown in FIG. 12 as a function of blood glucose concentration (mg/dl).

EXAMPLE 22

Figure 13:
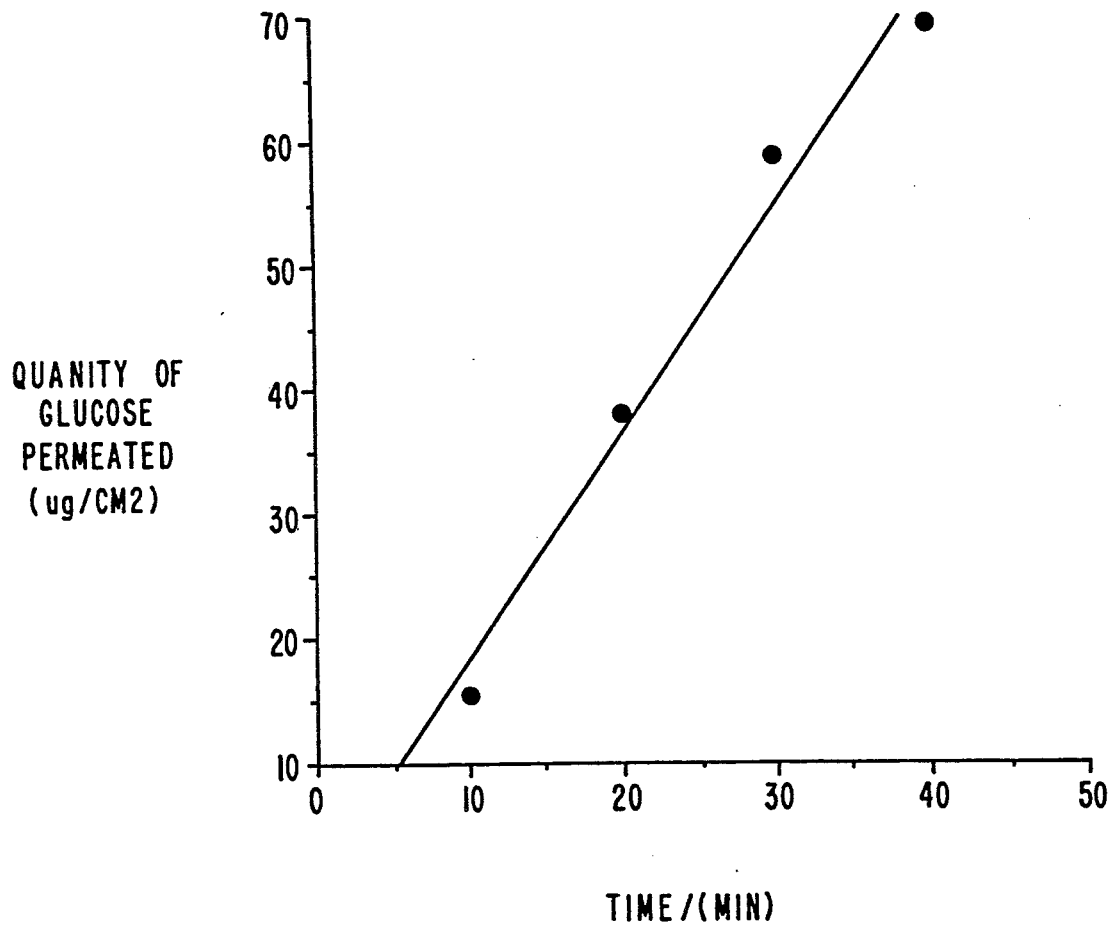
FIG. 13 is a graph of glucose permeated ($\mu$g/cm$^2$) verses time for the results of Example 22.

In this example, blood glucose was monitored noninvasively in a laboratory dog using a hydrogel. The hydrogel was prepared according to the procedure of Example 18, except that the concentration of sodium cholate in the hydrogel was 8%. Six hydrogel slices were placed on the buccal mucosa of a laboratory dog as described in Example 18. Two hydrogel slices were removed after 10, 20, and 30 minutes, respectively, and analyzed according to the procedure of Example 18. The blood glucose level in the dog was about 136.8 mg/dl during the procedure. The total amount of glucose permeated into the hydrogel, normalized to $\mu g/cm^2$, verses time is shown in FIG. 13. The lag time was determined to be 2-7 minutes.

EXAMPLE 23

Figure 14:
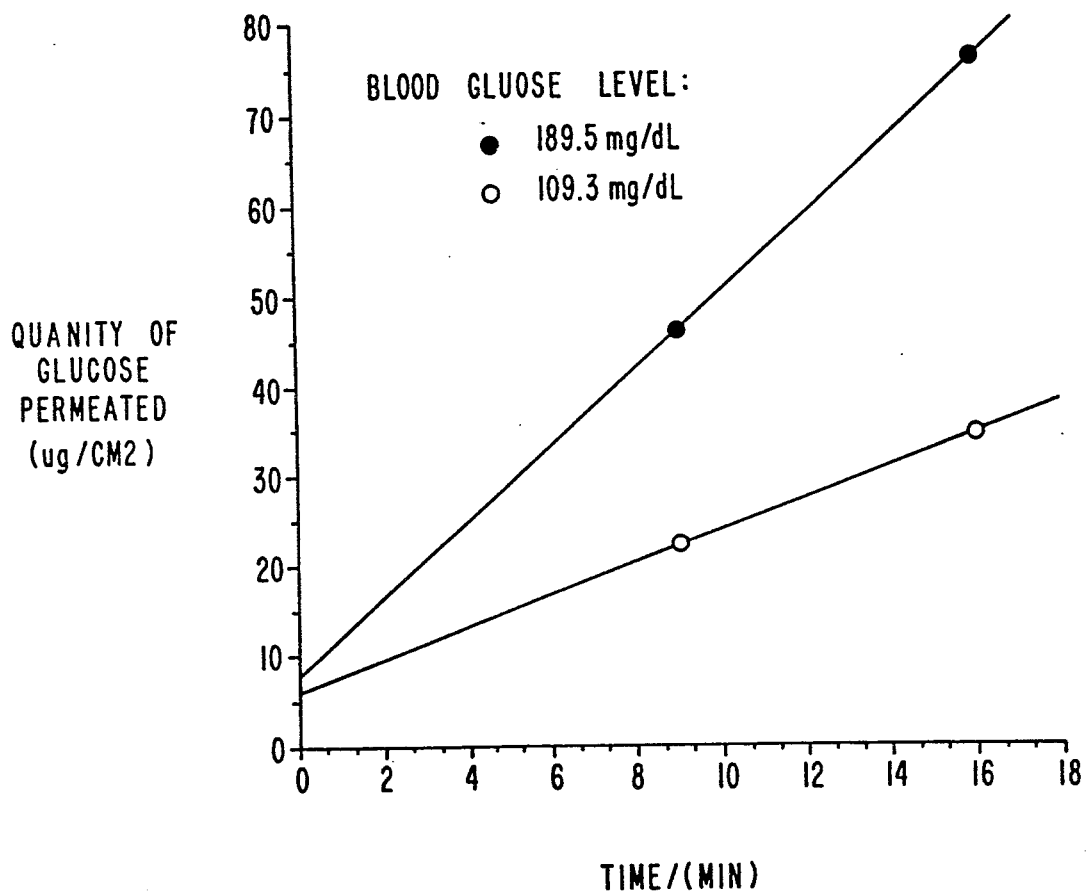
FIG. 14 is a graph of glucose permeated ($\mu$g/cm$^2$) verses time for the results of Examples 23 and 24.

In this example, blood glucose was monitored noninvasively in a laboratory dog using a hydrogel. The hydrogel was prepared according to the procedure of Example 18, except that the concentration of sodium cholate in the hydrogel was 16%. In addition, the hydrogel slices were removed after 9 minutes and 16 minutes, rather than 30 and 60 minutes. The blood glucose level in the dog was about 109.3 mg/dl during the procedure. The total amount of glucose permeated into the hydrogel, normalized to $\mu g/cm^2$, verses time is shown in FIG. 14. The lag time was negligible.

EXAMPLE 24

Blood glucose was monitored noninvasively in a laboratory dog using a hydrogel according to the procedure of Example 23, except that the blood glucose level was elevated according to the procedure described in Example 2. The same laboratory dog used in Example 23 was used in this Example. The blood glucose level in the dog was maintained about 189.5 mg/dl during the procedure. The total amount of glucose permeated into the hydrogel, normalized to $\mu g/cm^2$, verses time is also shown in FIG. 14.

EXAMPLE 25

Blood glucose was monitored noninvasively in a laboratory dog to determine the effect of surface area on glucose flux according to the procedure of Example 1, except that two differently sized diffusion cells were used. Each diffusion cell was placed on one side of the dog's mouth. Diffusion cell "A" had an open bottom area of 1.887 $cm^2$, while diffusion cell "B" had an area of 0.866 $cm^2$. The glucose flux for diffusion cell "A" was determined to be 4.87 $\mu g/minute/cm^2$, while the glucose flux for diffusion cell "B" was determined to be 4.80 $\mu g/minute/cm^2$. The results of Example 25 demonstrate that glucose flux is independent of surface area.

EXAMPLE 26

Blood glucose was monitored noninvasively in a laboratory dog using a diffusion cell and a hydrogel according to the procedures of Examples 1 and 18, respectively, except that the concentration of sodium cholate in both the glucose receiving solution and in the hydrogel was 8%.

Figure 15:
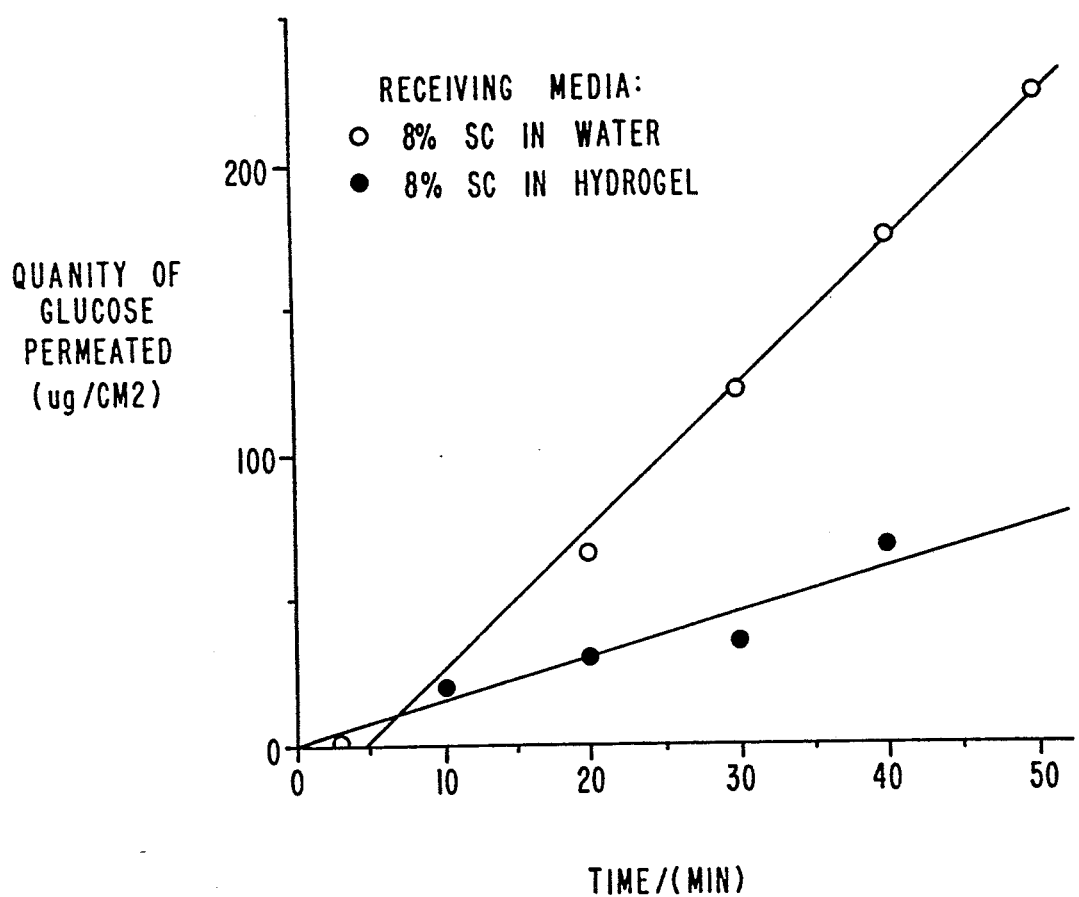
FIG. 15 is a graph of glucose permeated ($\mu$g/cm$^2$) verses time for the results of Example 26.

It was found that the total amount of glucose permeated over time was lower by a factor of about 3 using the hydrogel than with the diffusion cell. This result suggests that glucose permeating into the hydrogel is a rate limiting step when compared to the permeation of glucose across the mucosal membrane. Therefore, the results of Example 26 suggest that use of a hydrogel may provide a substantially uniform glucose permeation rate which is substantially independent of individual variations in mucosal membrane permeability. The hydrogel in Example 26 was acting as a rate regulating medium. The total amount of glucose permeated into the hydrogel, normalized to $\mu g/cm^2$, verses time is also shown in FIG. 15.

EXAMPLE 27

The solubility of glucose in various enhancer systems was determined by adding an excess amount of glucose to 5 ml of the tested enhancer system. After 15 minutes of sonication, the suspension was equilibrated for 3 days with shaking in a 32° C. water bath. The suspension was filtered through a Gelman ACRO LC13 filter (pore size, 0.2 $\mu m$), and the glucose concentration was determined by reverse-phase high pressure liquid chromatography ("HPLC"). The mobile phase was 80/16/2/2 $CH_3CN/H_2O/NH_4OH/CHCl_3$. The injection volume was 100 $\mu l$, and the flow rate was 2.0 ml/min at a column pressure of 1200 psi. A Whatman 11 cm×3.9 mm PartiSphere Polar Amino-Cyano column was used. The run time was from 5-7 minutes with a retention time of 3.4 minutes.

Figure 16:
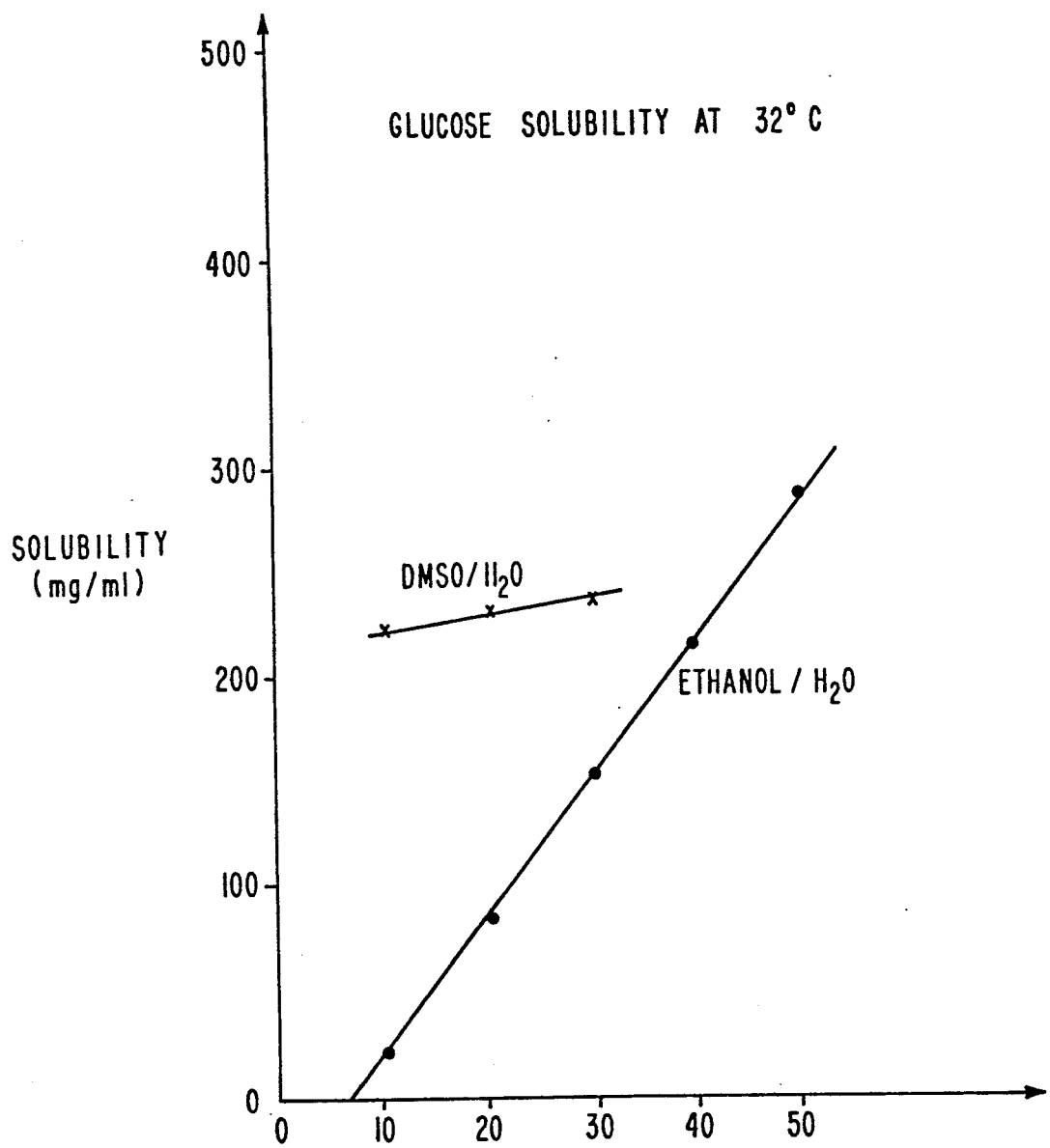
FIG. 16 is a graph of glucose solubility (mg/ml) verses water content for the results of Example 27.

Table III shows the solubility of glucose in ten different enhancer systems. In the $EtOH/H_2O$ and $DMSO/H_2O$ systems, glucose solubility is a linear function of $H_2O$ content in the enhancer formulations. It ranges from 22 mg/ml to 275 mg/ml in the $EtOH/H_2O$ systems and ranges form 223 mg/ml to 235 mg/ml in the $DMSO/H_2O$ systems. Glucose solubility data as a function of water content are presented in FIG. 16. In the 90/10 (40/60 ML/IPA)/$H_2O$ and 90/10 (40/60 GMO/IPA)/$H_2O$ systems, glucose solubilities are 9 and 7 mg/ml, respectively.

The enhancers with low glucose solubility will have a lower diffusion driving force for glucose back flux, resulting in lower quantities of glucose in the receiving medium.

TABLE III

| Solubility of Glucose in Various Enhancer Systems at 32° C. | |
|---|---|
| Glucose Receiving Medium | Solubility (mg/ml) |
| 1. 90/10 EtOH/$H_2O$ | 22 |
| 2. 80/20 EtOH/$H_2O$ | 86 |
| 3. 70/30 EtOH/$H_2O$ | 152 |
| 4. 60/40 EtOH/$H_2O$ | 212 |
| 5. 50/50 EtOH/$H_2O$ | 275 |
| 6. 90/10 DMSO/$H_2O$ | 223 |
| 7. 80/20 DMSO/$H_2O$ | 230 |
| 8. 70/30 DMSO/$H_2O$ | 235 |
| 9. 90/10 (40/60 ML*/IPA)/$H_2O$ | 9 |
| 10. 90/10 (40/60 GMO**/IPA)$H_2O$ | 7 |

*ML = Methyl Laurate
**GMO = Glyceryl Monooleate

EXAMPLE 28

In order to examine the feasibility of the novel glucose back-diffusion concept toward the design of noninvasive transdermal glucose sensors, the in vitro back-diffusion kinetics of glucose has been measured across the human cadaver skin at 32° C.

Figure 17:
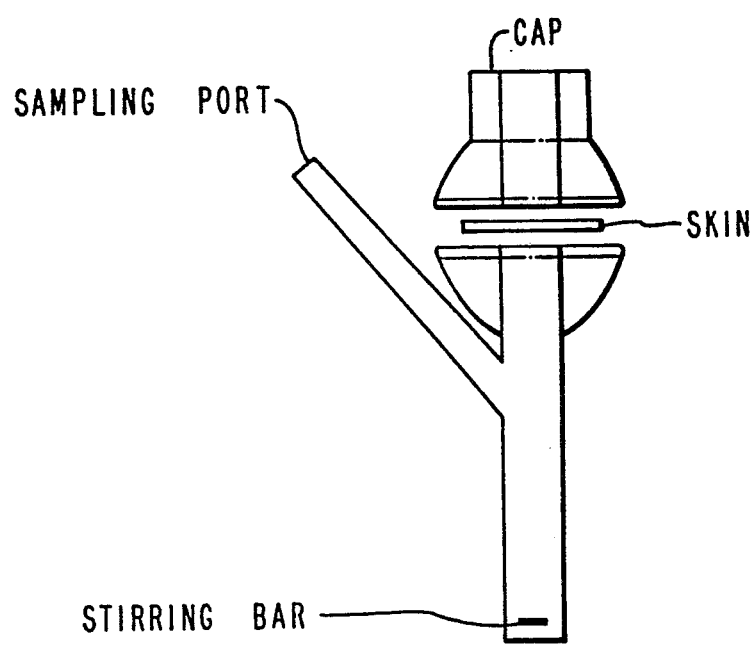
FIG. 17 is schematic view of a diffusion cell used to perform in vitro skin flux experiments.

The in vitro skin flux experiments were carried out using modified Franz diffusion cells such as those illustrated in FIG. 17. Human cadaver skin was heat separated at 60° C. for 1 minute and the epidermal layer was mounted between the donor and receptor compartments of the cells, the stratum corneum facing the receptor compartment. The diffusion cells were then placed in a heating/stirring module (Pierce Chemical-ReactiTherm ®) for temperature control and stirring of the donor compartment. The surface temperature of skin was maintained at 32°±1° C.

In this example, PBS saline containing a glucose concentration of 100 mg/ml, which is about 100 times higher than normal blood glucose level (~100 ml/dl), was introduced to the donor compartment which is the lower portion of the diffusion cell.

For the purpose of fluidizing the stratum corneum, which is the main barrier to the glucose permeation, and eliminating the lag time, a selected enhancer system from Table III was introduced to the receptor compartment for 24 hours. The receptor compartment was the upper portion of the diffusion cell illustrated in FIG. 17. The enhancer system was then replaced by the same, but fresh, enhancer formulation and the samples were taken afterwards.

The back-diffusion of glucose into the enhancer systems were measured at 1, 2, and 24 hours after pretreatment with the enhancer.

Glucose was analyzed using reverse phase HPLC. The mobile phase was 80/16/2/2 $CH_3CN/H_2O/NH_4OH/CHCl_3$. The injection volume was 100 $\mu l$, and the flow rate was 2.0 ml/min at a column pressure of 1200 psi. A Whatman 11 cm×3.9 mm PartiSphere Polar Amino-Cyano column was used. The run time was from 5-7 minutes with a retention time of 3.4 minutes.

This example was designed with the idea that a diabetic patient can apply a transdermal patch containing enhancer formulation to the test site on the body for a certain period of time before the blood glucose is read by another transdermal patch/sensor system.

Figure 18:
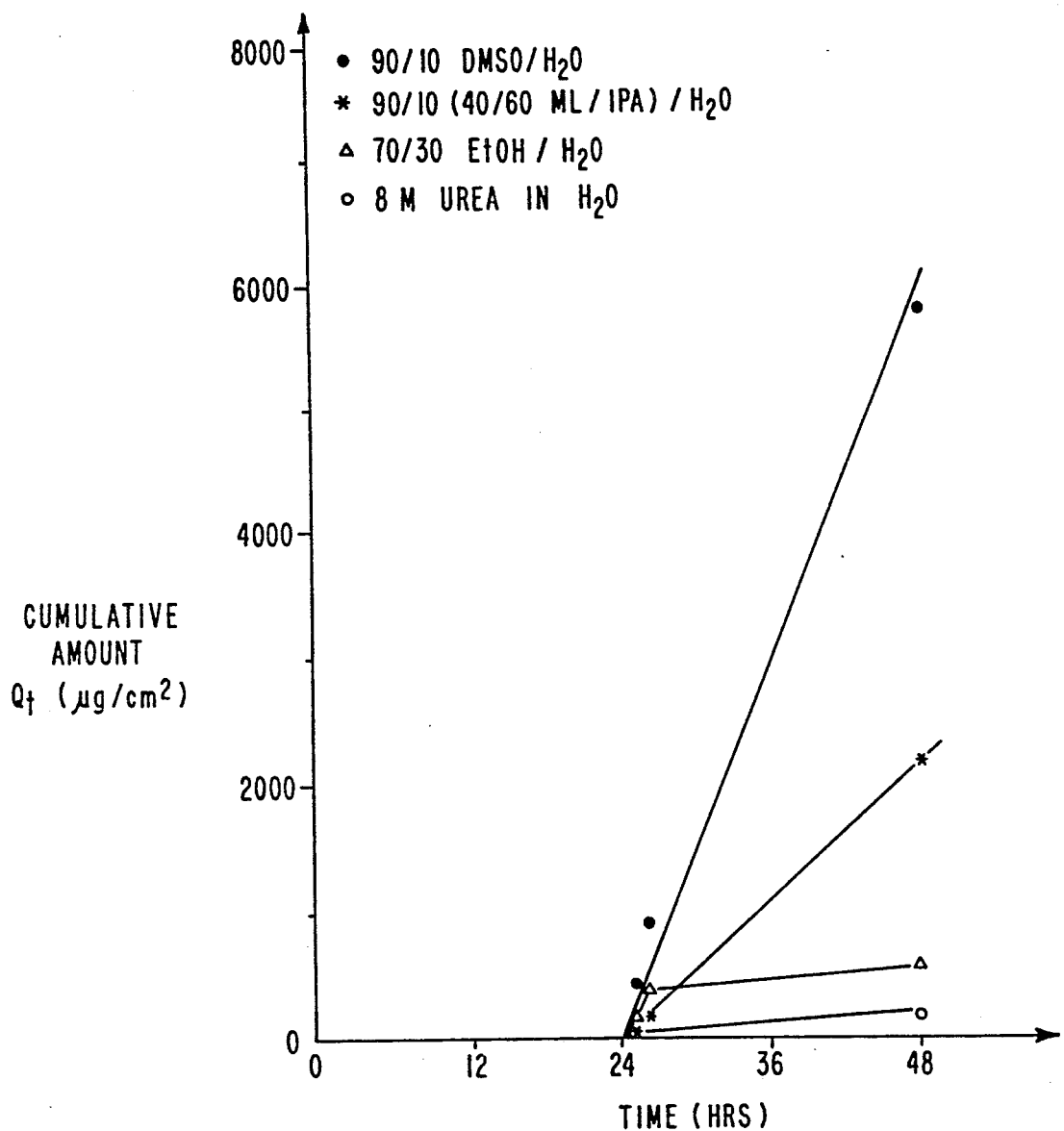
FIG. 18 is a graph of glucose permeated ($\mu$g/cm$^2$) verses time (hours) for the results of Example 28.

FIG. 18 shows the results obtained with four of the enhancer formulations identified in Table III (90/10 $DMSO/H_2O$, 90/10 (40/60 $ML/IPA)/H_2O$, 70/30 $EtOH/H_2O$, and 8M urea in $H_2O$). The cumulative amount of glucose back-diffusing across skin was determined with each formulation up to 24 hours after the pretreatment stage in 1 to 3 skin donor samples (each composition evaluated in triplicate per donor skin).

A steady-state flux of only 6.2 $\mu g/cm^2/hr$ was obtained with 8M urea/$H_2O$ system. 70/30 $EtOH/H_2O$, the enhancer formulation used in Estraderm ® patch, produced a steady-state flux of 167.6 $\mu g/cm^2/hr$ in the first 2 hours of study. However, the flux leveled off from 2 to 24 hours. This may be attributed to the ethanol depletion from the enhancer formulation. In contrast, 90/10 $DMSO/H_2O$ and 90/10 (40/60 $ML/IPA)/H_2O$ produced a steady-state flux rates of about 89 $\mu g/cm^2/hr$, respectively, for up to 24 hours.

EXAMPLE 29

Glucose skin flux determinations were made without pretreating the skin with an enhancer system. The skin was equilibrated with a glucose/PBS saline solution in the donor compartment for 4 hours. An enhancer system was then introduced to the receptor compartments at time, t=0. The amount of glucose permeating across the skin was measured at 4, 8, 20, 24, and 28 hours. At those sampling times, the receptor solutions (3 ml) were removed and glucose concentrations were determined by HPLC. The receptor solutions were replaced with the same, but fresh, enhancer formulations immediately and the caps were closely tightened to prevent the evaporation of enhancer ingredients.

The cumulative amounts of glucose permeating across the skin at time=t ($Q_t$, $\mu g/cm^2$) were determined using the following equation:

$$Q_t = \sum_{n=0}^{t} C_n \cdot V/S$$

Where "$C_n$" is the glucose concentration ($\mu g/ml$) determined by HPLC at time interval "t", "V" is the receptor volume (ml) and "S" is the surface area ($cm^2$). The steady-state flux, "$J_s$" ($\mu g/cm^2/hr$), was calculated from the linear slope of $Q_t$ verses t curve. By extrapolating the steady-state flux curve to the x-axis, the lag time, "$t_L$", was determined.

The in vitro skin flux experiments in this example were conducted under more realistic conditions than in Example 28. The glucose concentration in PBS saline was reduced from 100 mg/ml to 10 mg/ml and 1 mg/ml to mimic the hyperglycemic and normal blood level. The enhancer system was added to the receptor compartment and the samples were taken periodically without pretreating the skin. The purpose of this example was to determine the steady-state flux as well as the lag times required before reaching steady-state permeation.

Figure 19:
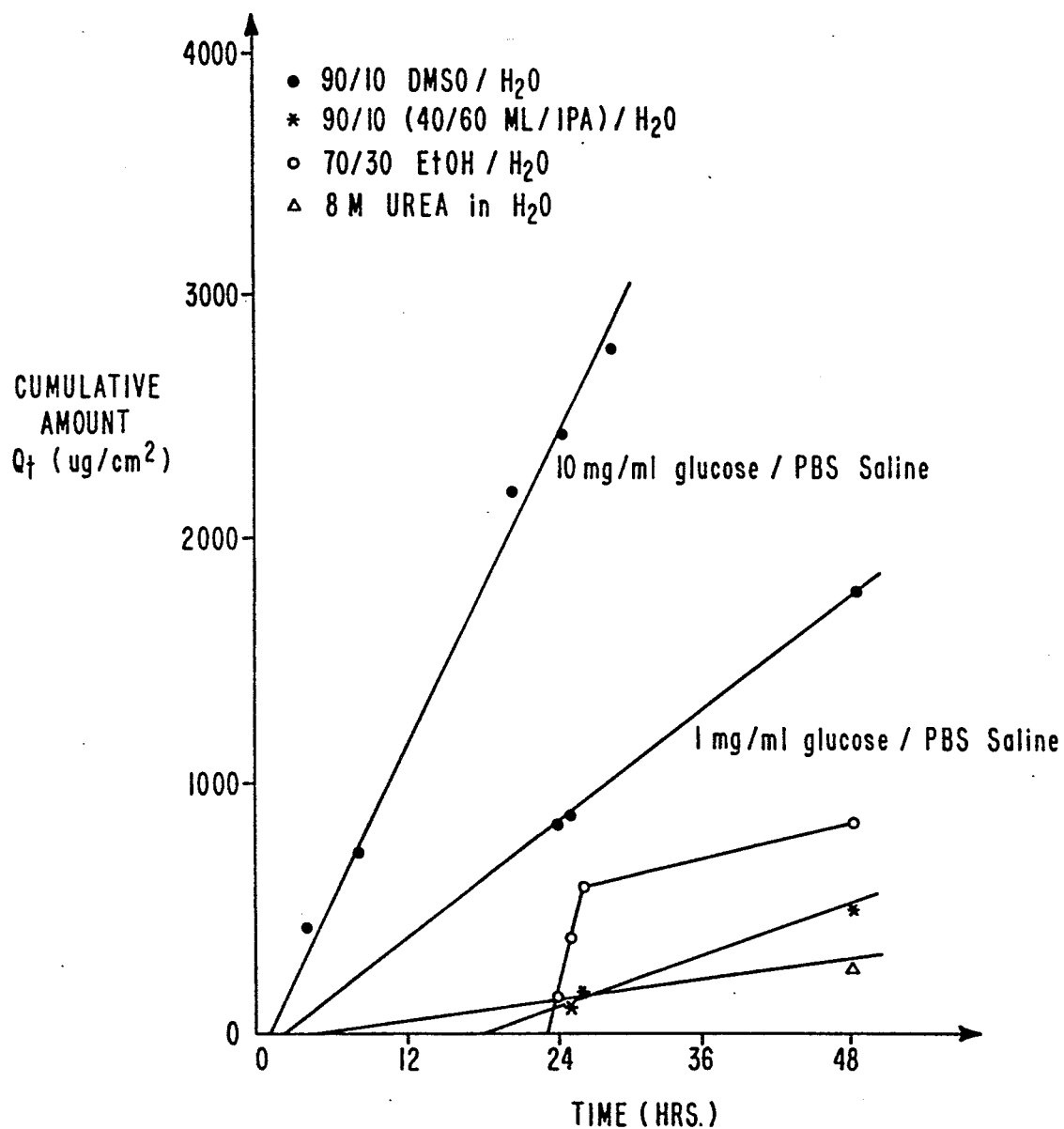
FIG. 19 is a graph of glucose permeated ($\mu$g/cm$^2$) verses time (hours) for the results of Example 29.

FIG. 19 shows the results obtained with the four enhancer systems used in Example 28 (90/10 $DMSO/H_2O$, 90/10 (40/60 $ML/IPA)/H_2O$, 70/30 $EtOH/H_2O$, and 8M urea in $H_2O$).

The glucose concentration was 1 mg/ml in the donor compartments and four enhancer systems were in the receptor compartments. In one study using 90/10 $DMSO/H_2O$, a glucose concentration of 10 mg/ml was employed as the donor solution. In the case of 1 mg/ml glucose level, the steady-state flux rates ranged from 5.8 to 125.8 $\mu g/cm^2/hr$, with 70/30 $EtOH/H_2O$ producing the highest flux. However, 70/30 $EtOH/H_2O$ also generated the longest lag time, 23.2 hours. On the contrary, 90/10 $DMSO/H_2O$ produced time lags of approximately 1-2 hours. As anticipated, glucose back-flux was reduced by lowering the donor concentration from 10 mg/ml to 1 mg/ml. However, this flux reduction was substantially less than 10-fold.

Although highly speculative, it is possible that glucose back-diffuses via a pore pathway which is viscosity dependent. As the glucose concentration decreases, viscosity also decreases in the donor solution. Such a viscosity effect would increase the diffusion coefficient at 1 mg/ml relative to that of a 10 mg/ml, thus accounting for the unexpectedly high flux at 1 mg/ml relative to 10 mg/ml.

Table IV summarizes the results obtained from these in vitro skin flux studies. The average skin flux rate, lag time and skin permeability ($P_s$) are tabulated. A $P_s$ of $1.06 \times 10^{-5}$ cm/sec was obtained from 90/10 $DMSO/H_2O$ under physiological conditions (i.e., glucose concentration in the donor side is 1 mg/ml). The $P_s$ value of the enhancer treated skin was close to the epidermis/dermis permeability (i.e., a $P_s$ of around 1 to $5 \times 10^{-5}$ cm/sec) indicating that the barrier property of the stratum corneum was essentially abolished in this study.

Thus, by employing a rate-limiting membrane with a permeability coefficient $P_M < 1 \times 10^{-5}$ cm/sec, the glucose flux may be controlled by the rate-limiting membrane. By using a transdermal patch of about 10 $cm^2$ and a glucose sensor with detection limit of ~1 $\mu g/ml$, a noninvasive glucose sensor can be developed by this novel approach.

TABLE IV

Summary of In-Vitro Skin Flux Data

| Enhancer Systems | Glucose Conc. (mg/ml) | Flux (μg/cm²/hr) | Lag Time (hrs) | $P_s \times 10^6$ (cm/sec) |
|---|---|---|---|---|
| 90/10 DMSO/H₂O | 1 | 38.2 | 2.5 | 10.61 |
| 90/10 DMSO/H₂O | 10 | 101.3 | 1.0 | 2.81 |
| 90/10 DMSO/H₂O | 100 | 229.5 | — | 0.64 |
| 90/10 */H₂O | 1 | 15.7 | 19.0 | 4.36 |
| 90/10 */H₂O | 100 | 88.6 | — | 0.25 |
| 70/30 EtOH/H₂O | 1 | 125.8 | 23.2 | 34.94 |
| 70/30 EtOH/H₂O | 100 | 167.6 | — | 0.47 |
| 8M urea/H₂O | 1 | 5.8 | 5 | 1.61 |
| 8M urea/H₂O | 100 | 6.2 | — | 0.02 |

* = 40/60 methyl laurate/isopropyl alcohol

In summary, the present invention permits noninvasive blood glucose monitoring which can be performed nearly as rapidly as conventional monitoring techniques, but without the pain, inconvenience, and risks of current invasive techniques.

From the foregoing, it will be appreciated that the present invention provides apparatus and methods for noninvasive blood glucose monitoring which avoids the inconvenience and risks associated with traditional invasive blood glucose monitoring techniques.

Additionally the present invention provides apparatus and methods for noninvasive blood glucose monitoring which provide reproducible and accurate correlation with actual blood glucose levels.

The present invention also provides apparatus and methods for noninvasive blood glucose monitoring which provide rapid results in sufficient time to administer appropriate medication.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An apparatus for noninvasive blood glucose monitoring comprising:
   a quantity of glucose receiving medium comprising a permeation enhancer capable of increasing the glucose permeability across an epithelial membrane;
   means for supporting the glucose receiving medium comprising a housing defining a receiving chamber therein and an opening to said receiving chamber;
   means for temporarily positioning the glucose receiving medium against the epithelial membrane; and
   a handle attached to the housing to facilitate positioning of the apparatus against the epithelial membrane and removal of the apparatus.

2. An apparatus for noninvasive blood glucose monitoring as defined in claim 1, wherein the means for supporting the glucose receiving medium and the means for temporarily positioning the glucose receiving medium against the mucosal membrane comprise a hydrogel.

3. An apparatus for noninvasive blood glucose monitoring as defined in claim 1, wherein the permeation enhancer comprises a natural bile salt.

4. An apparatus for noninvasive blood glucose monitoring as defined in claim 1, wherein the glucose receiving medium comprises water.

5. An apparatus for noninvasive blood glucose monitoring as defined in claim 1, wherein the glucose receiving medium comprises a cream.

6. An apparatus for noninvasive blood glucose monitoring as defined in claim 1, wherein the glucose receiving medium comprises a suspension.

7. An apparatus for noninvasive blood glucose monitoring as defined in claim 1, wherein the glucose receiving medium comprises an emulsion.

8. An apparatus for noninvasive blood glucose monitoring as defined in claim 1, wherein the glucose receiving medium comprises a semisolid composition.

9. An apparatus for noninvasive blood glucose monitoring as defined in claim 1, wherein the glucose receiving medium comprises a composition capable of reacting with glucose to form a substantially insoluble product.

10. An apparatus for noninvasive blood glucose monitoring as defined in claim 1, further comprising means for regulating the glucose permeation rate in order to provide a calibrated permeation rate despite variations in glucose permeation from patient to patient and from time to time.

11. An apparatus for noninvasive blood glucose monitoring comprising:
    a quantity of glucose receiving medium comprising a permeation enhancer capable of increasing the glucose permeability across a mucosal membrane within a patient's mouth;
    means for supporting the glucose receiving medium;
    means for temporarily positioning the glucose receiving medium against the mucosal membrane such that a quantity of glucose, which directly correlates on a real time basis with a patient's actual blood glucose value, is capable of permeating the mucosal membrane into the glucose receiving medium; and
    means for preventing contamination of the glucose receiving medium by saliva and other fluids present in the patient's mouth.

12. An apparatus for noninvasive blood glucose monitoring as defined in claim 11, wherein the means for supporting the glucose receiving medium comprises a housing defining a receiving chamber therein and an opening to said receiving chamber.

13. An apparatus for noninvasive blood glucose monitoring comprising:
    a quantity of glucose receiving medium comprising a permeation enhancer capable of increasing the glucose permeability across a mucosal membrane;
    means for supporting the glucose receiving medium comprising a housing defining a receiving chamber therein and an opening to said receiving chamber;
    means for temporarily positioning the glucose receiving medium against the mucosal membrane; and
    a handle attached to the housing to facilitate positioning of the apparatus against the mucosal membrane and removal of the apparatus.

14. An apparatus for noninvasive blood glucose monitoring as defined in claim 12, further comprising means for accessing the receiving chamber such that glucose receiving medium may be introduced into the receiving chamber or removed therefrom while the housing is positioned against the mucosal membrane.

15. An apparatus for noninvasive blood glucose monitoring as defined in claim 11, wherein the means for supporting the glucose receiving medium and the means for temporarily positioning the glucose receiving medium against the mucosal membrane comprise a hydrogel.

16. An apparatus for noninvasive blood glucose monitoring as defined in claim 15, wherein the hydrogel comprises hydroxypropylcellulose.

17. An apparatus for noninvasive blood glucose monitoring as defined in claim 15, wherein the hydrogel comprises carbopol.

18. An apparatus for noninvasive blood glucose monitoring as defined in claim 11, wherein the permeation enhancer comprises a natural bile salt.

19. An apparatus for noninvasive blood glucose monitoring as defined in claim 11, wherein the permeation enhancer comprises sodium cholate.

20. An apparatus for noninvasive blood glucose monitoring as defined in claim 11, wherein the permeation enhancer comprises sodium dodecyl sulfate.

21. An apparatus for noninvasive blood glucose monitoring as defined in claim 11, wherein the permeation enhancer comprises sodium deoxycholate.

22. An apparatus for noninvasive blood glucose monitoring as defined in claim 11, wherein the permeation enhancer comprises taurodeoxycholate.

23. An apparatus for noninvasive blood glucose monitoring as defined in claim 11, wherein the permeation enhancer comprises sodium glycocholate.

24. An apparatus for noninvasive blood glucose monitoring as defined in claim 11, wherein the permeation enhancer comprises a fatty acid.

25. An apparatus for noninvasive blood glucose monitoring as defined in claim 11, wherein the permeation enhancer comprises a saturated fatty acid.

26. An apparatus for noninvasive blood glucose monitoring as defined in claim 11, wherein the permeation enhancer comprises an unsaturated fatty acid.

27. An apparatus for noninvasive blood glucose monitoring as defined in claim 11, wherein the permeation enhancer comprises a surfactant.

28. An apparatus for noninvasive blood glucose monitoring as defined in claim 11, wherein the permeation enhancer comprises an ionic surfactant.

29. An apparatus for noninvasive blood glucose monitoring as defined in claim 11, wherein the permeation enhancer comprises a nonionic surfactant.

30. An apparatus for noninvasive blood glucose monitoring as defined in claim 11, wherein the permeation enhancer comprises a synthetic permeation enhancer.

31. An apparatus for noninvasive blood glucose monitoring as defined in claim 11, wherein the glucose receiving medium comprises water.

32. An apparatus for noninvasive blood glucose monitoring as defined in claim 11, wherein the glucose receiving medium comprises a cream.

33. An apparatus for noninvasive blood glucose monitoring as defined in claim 11, wherein the glucose receiving medium comprises a suspension.

34. An apparatus for noninvasive blood glucose monitoring as defined in claim 11, wherein the glucose receiving medium comprises an emulsion.

35. An apparatus for noninvasive blood glucose monitoring as defined in claim 11, wherein the glucose receiving medium comprises a semisolid composition.

36. An apparatus for noninvasive blood glucose monitoring as defined in claim 11, wherein the glucose receiving medium comprises a composition capable of reacting with glucose to form a substantially insoluble product.

37. An apparatus for noninvasive blood glucose monitoring as defined in claim 11, further comprising means for regulating the glucose permeation rate in order to provide a calibrated permeation rate despite variations in glucose permeation from patient to patient and from time to time.

38. An apparatus for noninvasive blood glucose monitoring comprising:
  a quantity of glucose receiving medium comprising a permeation enhancer capable of increasing the glucose permeability across skin;
  means for supporting the glucose receiving medium comprising a housing defining a receiving chamber therein and an opening to said receiving chamber;
  means for temporarily positioning the glucose receiving medium against the skin; and
  means for accessing the receiving chamber such that glucose receiving medium may be introduced into the receiving chamber or removed therefrom while the housing is positioned against the skin.

39. An apparatus for noninvasive blood glucose monitoring as defined in claim 38, wherein the permeation enhancer comprises a natural bile salt.

40. An apparatus for noninvasive blood glucose monitoring as defined in claim 38, wherein the permeation enhancer comprises DMSO.

41. An apparatus for noninvasive blood glucose monitoring as defined in claim 38, wherein the permeation enhancer comprises ethanol.

42. An apparatus for noninvasive blood glucose monitoring as defined in claim 38, wherein the permeation enhancer comprises a fatty acid.

43. An apparatus for noninvasive blood glucose monitoring as defined in claim 38, wherein the permeation enhancer comprises a surfactant.

44. An apparatus for noninvasive blood glucose monitoring as defined in claim 38, wherein the permeation enhancer comprises a synthetic permeation enhancer.

45. An apparatus for noninvasive blood glucose monitoring as defined in claim 38, wherein the glucose receiving medium comprises water.

46. An apparatus for noninvasive, blood glucose monitoring as defined in claim 38, wherein the glucose receiving medium comprises a cream.

47. An apparatus for noninvasive blood glucose monitoring as defined in claim 38, wherein the glucose receiving medium comprises a suspension.

48. An apparatus for noninvasive blood glucose monitoring as defined in claim 38, wherein the glucose receiving medium comprises an emulsion.

49. An apparatus for noninvasive blood glucose monitoring as defined in claim 38, wherein the glucose receiving medium comprises a semisolid composition.

50. An apparatus for noninvasive blood glucose monitoring as defined in claim 38, wherein the glucose receiving medium comprises a composition capable of reacting with glucose to form a substantially insoluble product.

51. An apparatus for noninvasive blood glucose monitoring as defined in claim 38, further comprising means for regulating the glucose permeation rate in order to provide a calibrated permeation rate despite variations in glucose permeation from patient to patient and from time to time.

52. An apparatus for noninvasive blood glucose monitoring comprising:
- a housing defining a receiving chamber therein and an opening to said receiving chamber;
- a quantity of glucose receiving medium located within the receiving chamber, said glucose receiving medium comprising a permeation enhancer capable of increasing the glucose permeability across a mucosal membrane within a patient's mouth;
- means for temporarily positioning the housing against the mucosal membrane, such that the opening to the receiving chamber is positioned over the mucosal membrane such that a quantity of glucose, which directly correlates on a real time basis with a patient's actual blood glucose value, is capable of permeating the mucosal membrane into the glucose receiving medium; and
- means for preventing contamination of the glucose receiving medium by saliva and other fluids present in the patient's mouth.

53. An apparatus for noninvasive blood glucose monitoring as defined in claim 52, wherein the glucose receiving medium comprises water.

54. An apparatus for noninvasive blood glucose monitoring as defined in claim 52, wherein the glucose receiving medium comprises a hydrogel.

55. An apparatus for noninvasive blood glucose monitoring as defined in claim 52, wherein the glucose receiving medium comprises a semisolid composition.

56. An apparatus for noninvasive blood glucose monitoring as defined in claim 52, wherein the glucose receiving medium comprises a composition capable of reacting with glucose to form a substantially insoluble product.

57. An apparatus for noninvasive blood glucose monitoring as defined in claim 52, further comprising means for regulating the glucose permeation rate in order to provide a calibrated permeation rate despite variations in glucose permeation from patient to patient and from time to time.

58. An apparatus for noninvasive blood glucose monitoring as defined in claim 52, wherein the permeation enhancer comprises a natural bile salt.

59. An apparatus for noninvasive blood glucose monitoring as defined in claim 52, wherein the permeation enhancer comprises a synthetic permeation enhancer.

60. An apparatus for noninvasive blood glucose monitoring as defined in claim 52, further comprising means for accessing the receiving chamber such that glucose receiving medium may be introduced into the receiving chamber or removed therefrom while the housing is positioned against the epithelial membrane.

61. An apparatus for noninvasive blood glucose monitoring as defined in claim 52, wherein the epithelial membrane comprises a mucosal membrane.

62. An apparatus for noninvasive blood glucose monitoring as defined in claim 52, wherein the epithelial membrane comprises skin.

* * * * *

UNITED STATES PATENT AND TRADEMARK OFFICE
CERTIFICATE OF CORRECTION

PATENT NO. : 5,139,023

DATED : August 18, 1992

INVENTOR(S) : THEODORE H. STANLEY et al.

It is certified that error appears in the above-identified patent and that said Letters Patent is hereby corrected as shown below:

```
Title page, column 1, line 1, "METHOD" should be --METHODS--
Column 1, line 1, "METHOD" should be --METHODS--
Column 4  line 13, "verses" should be --versus--
Column 4, line 16, "verses" should be --versus--
Column 4, line 18, "verses" should be --versus--
Column 4, line 19, "verses" should be --versus--
Column 4, line 21, "verses" should be --versus--
Column 4, line 23, "verses" should be --versus--
Column 4, line 26, "verses" should be --versus--
Column 4, line 29, "verses" should be --versus--
Column 4, line 32, "verses" should be --versus--
Column 4, line 35, "verses" should be --versus--
Column 4, line 37, "verses" should be --versus--
Column 4, line 39, "verses" should be --versus--
Column 4, line 41, "verses" should be --versus--
Column 4, line 42, after "is" insert --a--
Column 4, line 45, "verses" should be --versus--
Column 5, line 68, "than" should be --then--
Column 7, line 61, "some" should be --same--
Column 15, line 47, "obtaining" should be --obtained--
Column 15, line 64, "verses" should be --versus--
Column 17, line 7, "verses" should be --versus--
Column 17, line 20, "verses" should be --versus--
Column 17, line 33, "verses" should be --versus--
```

UNITED STATES PATENT AND TRADEMARK OFFICE
CERTIFICATE OF CORRECTION

PATENT NO. : 5,139,023

DATED : August 18, 1992

INVENTOR(S) : THEODORE H. STANLEY et al.

It is certified that error appears in the above-identified patent and that said Letters Patent is hereby corrected as shown below:

```
Column 18, line 1, "verses" should be --versus--
Column 20, line 10, "verses" should be --versus--
```

Signed and Sealed this

Twenty-sixth Day of December, 1995

*Attest:*

BRUCE LEHMAN

*Attesting Officer*    *Commissioner of Patents and Trademarks*